(12) United States Patent
Chaikof et al.

(10) Patent No.: US 9,035,028 B2
(45) Date of Patent: May 19, 2015

(54) TEMPERATURE SENSITIVE CONJUGATE COMPOSITIONS

(75) Inventors: Elliot L. Chaikof, Atlanta, GA (US); Karlheinz Peter, Hawthorne East (AU); Danijal Topcic, Highett (AU); Carolyn A. Haller, Wellesley, MA (US); Wookhyun Kim, Boston, MA (US)

(73) Assignees: Emory University, Atlanta, GA (US); Baker IDI Heart & Diabetes Institute Holdings Ltd., Melbourne (AU)

( * ) Notice: Subject to any disclaimer, the term of this patent is extended or adjusted under 35 U.S.C. 154(b) by 0 days.

(21) Appl. No.: 13/583,055

(22) PCT Filed: Mar. 8, 2011

(86) PCT No.: PCT/US2011/027498
§ 371 (c)(1),
(2), (4) Date: Oct. 17, 2012

(87) PCT Pub. No.: WO2011/112549
PCT Pub. Date: Sep. 15, 2011

(65) Prior Publication Data
US 2013/0034552 A1 Feb. 7, 2013

Related U.S. Application Data

(60) Provisional application No. 61/339,867, filed on Mar. 10, 2010.

(51) Int. Cl.
| | |
|---|---|
| C12P 21/08 | (2006.01) |
| A61K 38/17 | (2006.01) |
| A61K 47/48 | (2006.01) |
| C07K 14/78 | (2006.01) |
| C07K 16/28 | (2006.01) |

(52) U.S. Cl.
CPC ......... *A61K 47/48246* (2013.01); *C07K 14/78* (2013.01); *C07K 16/2848* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,643,681 A | * | 7/1997 | Voorhees et al. | 428/483 |
| 5,854,387 A | * | 12/1998 | Urry et al. | 530/323 |
| 5,972,406 A | * | 10/1999 | Urry et al. | 426/549 |
| 2004/0171545 A1 | * | 9/2004 | Chaikof et al. | 514/12 |
| 2010/0048473 A1 | * | 2/2010 | Chaikof et al. | 514/12 |

FOREIGN PATENT DOCUMENTS

| | | |
|---|---|---|
| WO | 90-14103 A1 | 11/1990 |
| WO | 2006-1102922 A2 | 10/2006 |
| WO | 2009-140598 A1 | 11/2009 |

OTHER PUBLICATIONS

Megeed Z. et al. Biomacro-molecules, 7(4):999-1004, Apr. 2006.*
International Search Report for PCT/US2011/027498, mailed Nov. 25, 2011.

* cited by examiner

*Primary Examiner* — Robert Landsman
(74) *Attorney, Agent, or Firm* — Emory Patent Group

(57) ABSTRACT

This disclosure relates to temperature sensitive conjugates, compositions, and uses related thereto. In certain embodiments, the disclosure relates to conjugate polymers comprising a) a temperature sensitive polymer and b) an antibody. Typically the antibody has an epitope to a platelet receptor. The antibody may be a single-chain antibody wherein the platelet receptor is GPIIb/IIIa, such as an anti-GPIIb/IIIa antibody. In certain embodiments, the antibody binds specifically to the activated conformation of GPIIb/IIIa, i.e., an activation-specific GPIIb/IIIa antibody.

8 Claims, 13 Drawing Sheets

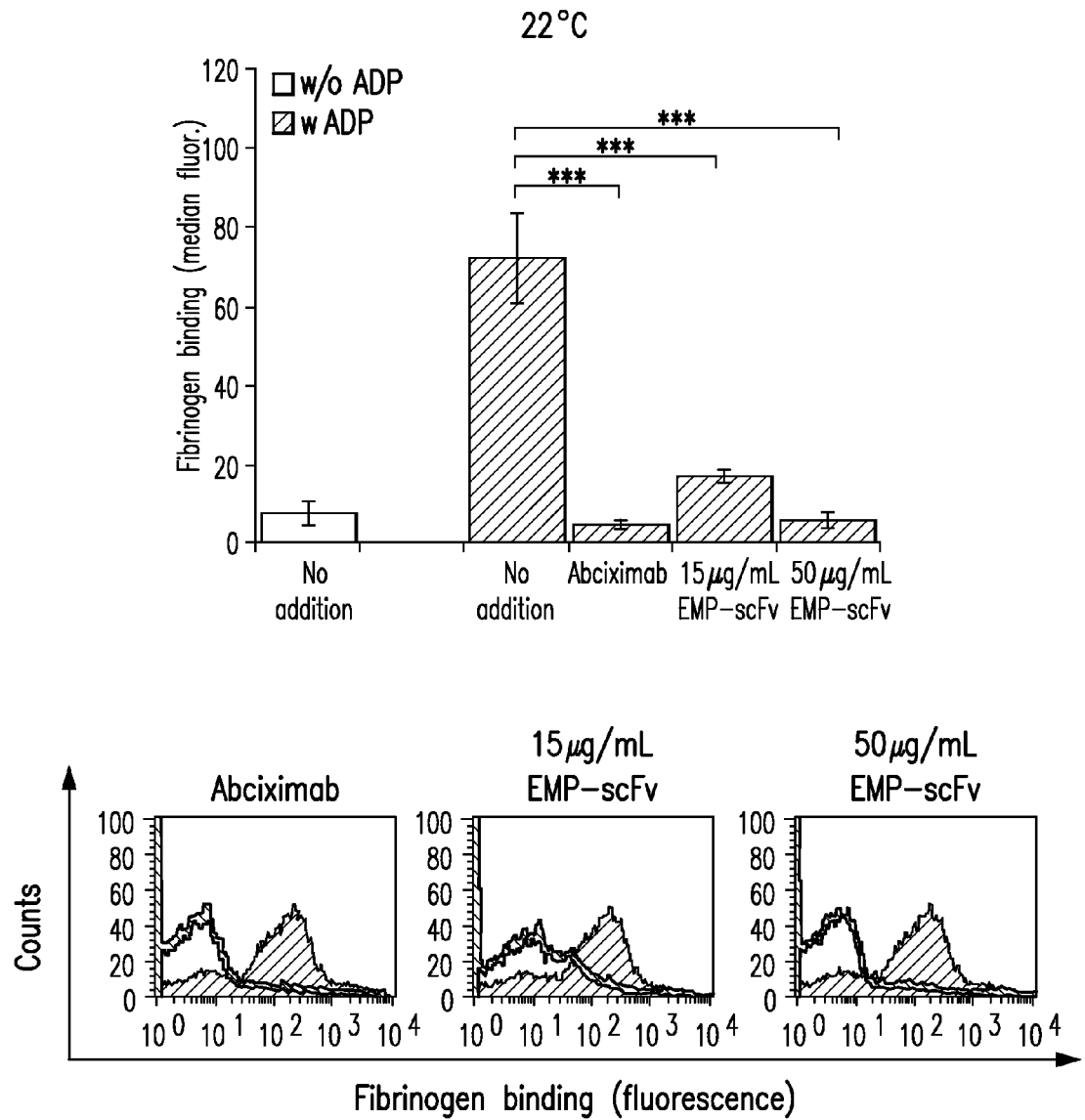
FIG. 4B1

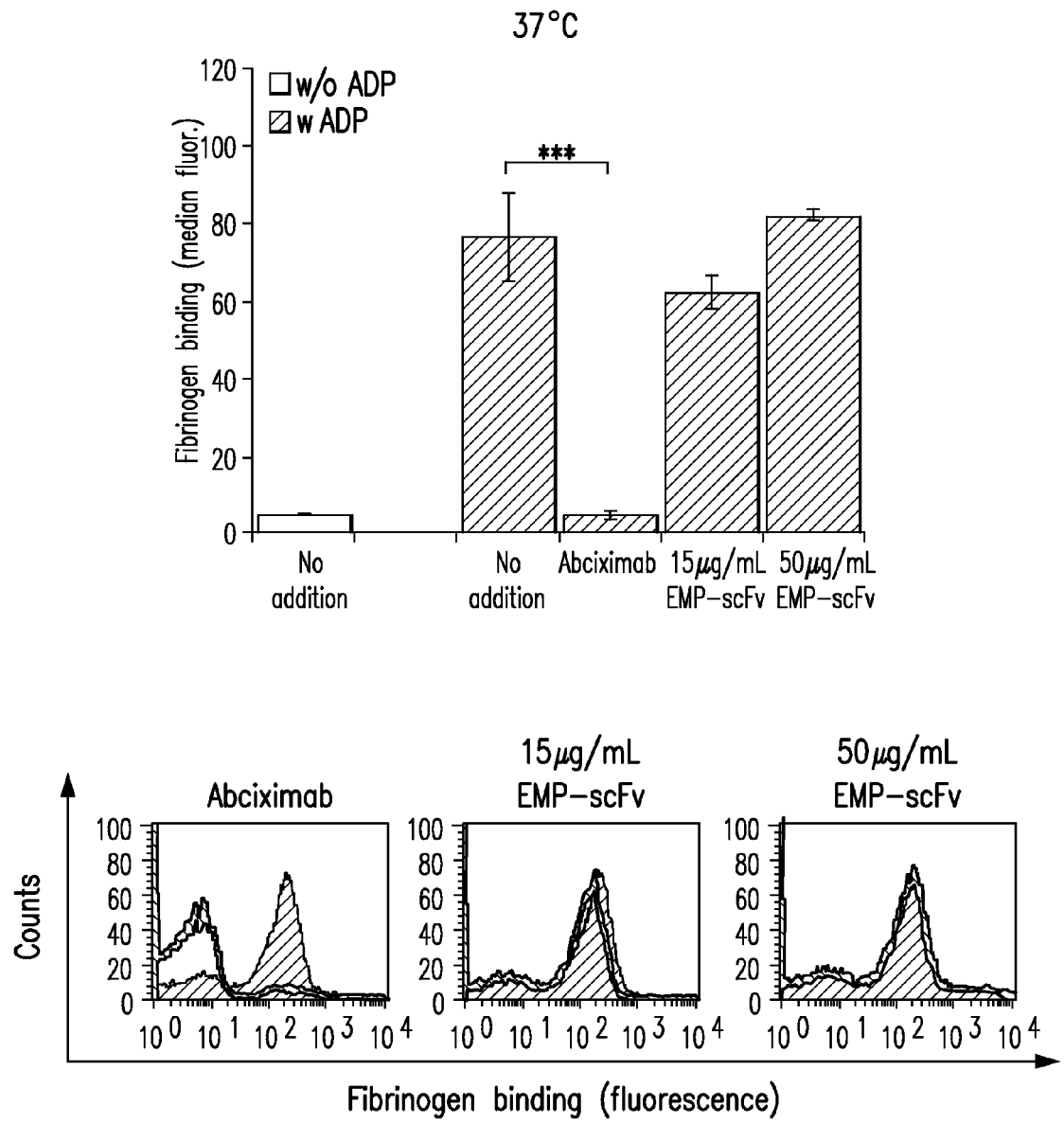
FIG. 4B2

SEQUENCE LISTING

<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: Xaa
<222> LOCATION: (1)..(1)
<223> OTHER INFORMATION: Xaa is Gly, Ala, Leu, Ile or Val
<220> FEATURE:
<221> NAME/KEY: Xaa
<222> LOCATION: (3)..(3)
<223> OTHER INFORMATION: Xaa is Gly, Ala, Leu, Ile or Val
<220> FEATURE:
<221> NAME/KEY: Xaa
<222> LOCATION: (4)..(4)
<223> OTHER INFORMATION: Xaa can be any amino acid except Pro
<220> FEATURE:
<221> NAME/KEY: Xaa
<222> LOCATION: (4)..(4)
<223> OTHER INFORMATION: Xaa is valine or histidine
<220> FEATURE:
<221> NAME/KEY: Xaa
<222> LOCATION: (4)..(4)
<223> OTHER INFORMATION: Xaa is Gly, Ala, Leu, Ile or Val
<220> FEATURE:
<221> NAME/KEY: Xaa
<222> LOCATION: (5)..(5)
<223> OTHER INFORMATION: Xaa is Gly, Ala, Leu, Ile or Val

<400> SEQUENCE: 1

Xaa Pro Xaa Xaa Xaa
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic construct

<400> SEQUENCE: 2

Val Pro Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Val Pro Gly Val Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Val Pro Ala Val Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

Ala Pro Gly Val Gly Val
1               5

<210> SEQ ID NO 6
<211> LENGTH: 75
<212> TYPE: DNA
<213> ORGANISM: Artificial Sequence
<220> FEATURE:
<223> OTHER INFORMATION: Synthetic construct

<400> SEQUENCE: 6
attccggctg ttggtatccc agctgttggt atcccagctg ttggcattcc ggctgtaggt    60
atcccggcag tgggc                                                    75

<210> SEQ ID NO 7
<211> LENGTH: 1212
<212> TYPE: DNA
<213> ORGANISM: Artificial Sequence
<220> FEATURE:
<223> OTHER INFORMATION: Synthetic construct

<400> SEQUENCE: 7

```
atggcggttc cagctgttgg tattccggct gttggtatcc cagctgttgg tatcccagct    60
gttggcattc cggctgtagg tatcccggca gtgggcattc cggctgttgg tatcccagct   120
gttggtatcc cagctgttgg cattccggct gtaggtatcc cggcagtggg cattccggct   180
gttggtatcc cagctgttgg tatcccagct gttggcattc cggctgtagg tatcccggca   240
gtgggcattc cggctgttgg tatcccagct gttggtatcc cagctgttgg cattccggct   300
gtaggtatcc cggcagtggg cattccggct gttggtatcc cagctgttgg tatcccagct   360
gttggcattc cggctgtagg tatcccggca gtgggcattc cggctgttgg tatcccagct   420
gttggtatcc cagctgttgg cattccggct gtaggtatcc cggcagtggg cattccggct   480
gttggtatcc cagctgttgg tatcccagct gttggcattc cggctgtagg tatcccggca   540
gtgggcattc cggctgttgg tatcccagct gttggtatcc cagctgttgg cattccggct   600
gtaggtatcc cggcagtggg cattccggct gttggtatcc cagctgttgg tatcccagct   660
gttggcattc cggctgtagg tatcccggca gtgggcattc cggctgttgg tatcccagct   720
gttggtatcc cagctgttgg cattccggct gtaggtatcc cggcagtggg cattccggct   780
gttggtatcc cagctgttgg tatcccagct gttggcattc cggctgtagg tatcccggca   840
gtgggcattc cggctgttgg tatcccagct gttggtatcc cagctgttgg cattccggct   900
gtaggtatcc cggcagtggg cattccggct gttggtatcc cagctgttgg tatcccagct   960
gttggcattc cggctgtagg tatcccggca gtgggcattc cggctgttgg tatcccagct  1020
gttggtatcc cagctgttgg cattccggct gtaggtatcc cggcagtggg cattccggct  1080
gttggtatcc cagctgttgg tatcccagct gttggcattc cggctgtagg tatcccggca  1140
gtgggcattc cggctgttgg tatcccagct gttggtatcc cagctgttgg cattccggct  1200
gtaggtattc ca                                                      1212

<210> SEQ ID NO 8
<211> LENGTH: 18
<212> TYPE: DNA
<213> ORGANISM: Artificial Sequence
<220> FEATURE:
<223> OTHER INFORMATION: Synthetic construct

<400> SEQUENCE: 8
ggtggcggtg gctccatg                                                 18

<210> SEQ ID NO 9
<211> LENGTH: 864
<212> TYPE: DNA
<213> ORGANISM: Artificial Sequence
<220> FEATURE:
<223> OTHER INFORMATION: Synthetic construct

<400> SEQUENCE: 9
atggcggagg tgcagctggt ggagtctggg ggaggcttgg tacagcctgg ggggtccctg    60
agactctcct gtgcagcctc tggattcatg tttagcaggt atgccatgag ctgggtccgc   120
caggctccag ggaaggggcc agagtgggtc tcaggtatta gtggtagtgg tggtagtaca   180
tactacgcag actccgtgaa gggccggttc accgtctcca gagacaattc caagaacacg   240
ctgtatctgc aaatgaacag cctgagagcc gaggacactg ccgtgtatta ctgtgcgaga   300
atttttacgc atcggtcgcg tggtgacgtc ccggaccaaa ctagctttga ctactggggc   360
cagggaaccc tggtcaccgt ctcctcaggg agtgcatccg ccccaaagct tgaagaaggt   420
gaattttcag aagcacgcgt aagctctgaa ctgactcagg accctgctgt gtctgtggcc   480
```

```
ttgggacaga cagtcaggat cacatgccaa ggagacagcc tcagaaactt ttatgcaagc    540
tggtaccagc agaagccagg acaggcccct actcttgtca tctatggttt aagtaaaagg    600
ccctcaggga tcccagaccg attctctgcc tccagctcag gaaacacagc ttccttgacc    660
atcactgggg ctcaggcgga agatgaggct gattattact gcctgctcta ctatggtggt    720
ggtcagcagg gagtgttcgg cggagggacc aagctgaccg tcctacgtca gcccaaggct    780
gccccctcgg tcactctgtt cccgccctct tctgcggccg ctggatccga acaaaagctg    840
atctcagaag aagacctaaa ctca                                           864
```

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10

```
catcaccatc accatcacta a                                               21
```

<210> SEQ ID NO 11
<211> LENGTH: 404
<212> TYPE: PRT
<213> ORGANISM: Artificial Sequence
<220> FEATURE:
<223> OTHER INFORMATION: Synthetic construct

<400> SEQUENCE: 11

```
Met Ala Val Pro Ala Val Gly Ile Pro Ala Val Gly Ile Pro Ala Val
 1               5                  10                  15

Gly Ile Pro Ala Val Gly Ile Pro Ala Val Gly Ile Pro Ala Val Gly
            20                  25                  30

Ile Pro Ala Val Gly Ile Pro Ala Val Gly Ile Pro Ala Val Gly Ile
        35                  40                  45

Pro Ala Val Gly Ile Pro Ala Val Gly Ile Pro Ala Val Gly Ile Pro
    50                  55                  60

Ala Val Gly Ile Pro Ala Val Gly Ile Pro Ala Val Gly Ile Pro Ala
65                  70                  75                  80

Val Gly Ile Pro Ala Val Gly Ile Pro Ala Val Gly Ile Pro Ala Val
                85                  90                  95

Gly Ile Pro Ala Val Gly Ile Pro Ala Val Gly Ile Pro Ala Val Gly
            100                 105                 110

Ile Pro Ala Val Gly Ile Pro Ala Val Gly Ile Pro Ala Val Gly Ile
        115                 120                 125

Pro Ala Val Gly Ile Pro Ala Val Gly Ile Pro Ala Val Gly Ile Pro
    130                 135                 140

Ala Val Gly Ile Pro Ala Val Gly Ile Pro Ala Val Gly Ile Pro Ala
145                 150                 155                 160

Val Gly Ile Pro Ala Val Gly Ile Pro Ala Val Gly Ile Pro Ala Val
                165                 170                 175

Gly Ile Pro Ala Val Gly Ile Pro Ala Val Gly Ile Pro Ala Val Gly
            180                 185                 190

Ile Pro Ala Val Gly Ile Pro Ala Val Gly Ile Pro Ala Val Gly Ile
        195                 200                 205

Pro Ala Val Gly Ile Pro Ala Val Gly Ile Pro Ala Val Gly Ile Pro
    210                 215                 220
```

```
Ala Val Gly Ile Pro Ala Val Gly Ile Pro Ala Val Gly Ile Pro Ala
225                 230                 235                 240
Val Gly Ile Pro Ala Val Gly Ile Pro Ala Val Gly Ile Pro Ala Val
                245                 250                 255
Gly Ile Pro Ala Val Gly Ile Pro Ala Val Gly Ile Pro Ala Val Gly
            260                 265                 270
Ile Pro Ala Val Gly Ile Pro Ala Val Gly Ile Pro Ala Val Gly Ile
        275                 280                 285
Pro Ala Val Gly Ile Pro Ala Val Gly Ile Pro Ala Val Gly Ile Pro
    290                 295                 300
Ala Val Gly Ile Pro Ala Val Gly Ile Pro Ala Val Gly Ile Pro Ala
305                 310                 315                 320
Val Gly Ile Pro Ala Val Gly Ile Pro Ala Val Gly Ile Pro Ala Val
                325                 330                 335
Gly Ile Pro Ala Val Gly Ile Pro Ala Val Gly Ile Pro Ala Val Gly
            340                 345                 350
Ile Pro Ala Val Gly Ile Pro Ala Val Gly Ile Pro Ala Val Gly Ile
        355                 360                 365
Pro Ala Val Gly Ile Pro Ala Val Gly Ile Pro Ala Val Gly Ile Pro
    370                 375                 380
Ala Val Gly Ile Pro Ala Val Gly Ile Pro Ala Val Gly Ile Pro Ala
385                 390                 395                 400

Val Gly Ile Pro

<210> SEQ ID NO 12
<211> LENGTH: 6
<212> TYPE: PRT
<213> ORGANISM: Artificial Sequence
<220> FEATURE:
<223> OTHER INFORMATION: Synthetic construct

<400> SEQUENCE: 12

Gly Gly Gly Gly Ser Met
1               5

<210> SEQ ID NO 13
<211> LENGTH: 288
<212> TYPE: PRT
<213> ORGANISM: Artificial Sequence
<220> FEATURE:
<223> OTHER INFORMATION: Synthetic construct

<400> SEQUENCE: 13

Met Ala Glu Val Gln Leu Val Glu Ser Gly Gly Leu Val Gln Pro
1               5                   10                  15
Gly Gly Ser Leu Arg Leu Ser Cys Ala Ala Ser Gly Phe Met Phe Ser
                20                  25                  30
Arg Tyr Ala Met Ser Trp Val Arg Gln Ala Pro Gly Lys Gly Pro Glu
            35                  40                  45
Trp Val Ser Gly Ile Ser Gly Ser Gly Gly Ser Thr Tyr Tyr Ala Asp
        50                  55                  60
Ser Val Lys Gly Arg Phe Thr Val Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Arg Ile Phe Thr His Arg Ser Arg Gly Asp Val Pro Asp
            100                 105                 110
```

```
Gln Thr Ser Phe Asp Tyr Trp Gly Gln Gly Thr Leu Val Thr Val Ser
            115                 120                 125
Ser Gly Ser Ala Ser Ala Pro Lys Leu Glu Gly Glu Phe Ser Glu
    130                 135                 140
Ala Arg Val Ser Ser Glu Leu Thr Gln Asp Pro Ala Val Ser Val Ala
145                 150                 155                 160
Leu Gly Gln Thr Val Arg Ile Thr Cys Gln Gly Asp Ser Leu Arg Asn
                165                 170                 175
Phe Tyr Ala Ser Trp Tyr Gln Gln Lys Pro Gly Gln Ala Pro Thr Leu
            180                 185                 190
Val Ile Tyr Gly Leu Ser Lys Arg Pro Ser Gly Ile Pro Asp Arg Phe
        195                 200                 205
Ser Ala Ser Ser Ser Gly Asn Thr Ala Ser Leu Thr Ile Thr Gly Ala
    210                 215                 220
Gln Ala Glu Asp Glu Ala Asp Tyr Tyr Cys Leu Leu Tyr Tyr Gly Gly
225                 230                 235                 240
Gly Gln Gln Gly Val Phe Gly Gly Gly Thr Lys Leu Thr Val Leu Arg
                245                 250                 255
Gln Pro Lys Ala Ala Pro Ser Val Thr Leu Phe Pro Pro Ser Ser Ala
            260                 265                 270
Ala Ala Gly Ser Glu Gln Lys Leu Ile Ser Glu Glu Asp Leu Asn Ser
        275                 280                 285

<210> SEQ ID NO 14
<211> LENGTH: 3
<212> TYPE: PRT
<213> ORGANISM: Artificial Sequence
<220> FEATURE:
<223> OTHER INFORMATION: Synthetic construct

<400> SEQUENCE: 14

Gly Val Pro
1

<210> SEQ ID NO 15
<211> LENGTH: 4
<212> TYPE: PRT
<213> ORGANISM: Artificial Sequence
<220> FEATURE:
<223> OTHER INFORMATION: Synthetic construct

<400> SEQUENCE: 15

Gly Gly Val Pro
1

<210> SEQ ID NO 16
<211> LENGTH: 5
<212> TYPE: PRT
<213> ORGANISM: Artificial Sequence
<220> FEATURE:
<223> OTHER INFORMATION: Synthetic construct

<400> SEQUENCE: 16

Pro Gly Val Gly Val
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic construct
```

```
<400> SEQUENCE: 17

Pro Gly Val Gly Val Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Ala Gly Val Pro Gly Phe Gly Val Gly
1               5

<210> SEQ ID NO 19
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: Xaa
<222> LOCATION: (2)..(2)
<223> OTHER INFORMATION: Xaa can be any amino acid except Pro
<220> FEATURE:
<221> NAME/KEY: Xaa
<222> LOCATION: (2)..(2)
<223> OTHER INFORMATION: Xaa is valine or histidine

<400> SEQUENCE: 19

Gly Xaa Gly
1

<210> SEQ ID NO 20
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: Xaa
<222> LOCATION: (4)..(4)
<223> OTHER INFORMATION: Xaa can be any amino acid except Pro
<220> FEATURE:
<221> NAME/KEY: Xaa
<222> LOCATION: (4)..(4)
<223> OTHER INFORMATION: Xaa can be Val or His

<400> SEQUENCE: 20

Val Pro Ala Xaa Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: Xaa
<222> LOCATION: (4)..(4)
<223> OTHER INFORMATION: Xaa can be any amino acid except Pro
<220> FEATURE:
<221> NAME/KEY: Xaa
<222> LOCATION: (4)..(4)
<223> OTHER INFORMATION: Xaa can be Val or His

<400> SEQUENCE: 21
```

-continued

```
Ala Pro Gly Xaa Ala Ala Gly
1               5

<210> SEQ ID NO 22
<211> LENGTH: 20
<212> TYPE: PRT
<213> ORGANISM: Artificial Sequence
<220> FEATURE:
<223> OTHER INFORMATION: Synthetic construct

<400> SEQUENCE: 22

Asp Tyr Pro Val Asp Ile Tyr Tyr Leu Met Asp Leu Ser Tyr Ser Met
1               5                   10                  15

Lys Asp Asp Leu
            20

<210> SEQ ID NO 23
<211> LENGTH: 5
<212> TYPE: PRT
<213> ORGANISM: Artificial Sequence
<220> FEATURE:
<223> OTHER INFORMATION: Synthetic construct

<400> SEQUENCE: 23

Ile Pro Ala Val Gly
1               5
```

TEMPERATURE SENSITIVE CONJUGATE COMPOSITIONS

This application claims priority to U.S. Provisional Application No. 61/339,867 filed on 10 Mar. 2010, hereby incorporated by reference.

BACKGROUND

Therapeutic hypothermia (TH) is widely used to reduce oxygen requirements and to protect organs from ischemia. In cardiac surgery hypothermia is typically established temporarily with the heart lung machine during cardiopulmonary bypass (CPB), and deep hypothermic circulatory arrest (DHCA) is an important component of surgery for congenital heart disease. DHCA is also used in adult patients for the repair of thoracic aortic dissections as well as in neurosurgical operations for the treatment of cerebral aneurysm.

TH employed in clinical settings has also been associated with platelet activation, aggregation, sequestration, and (micro)vascular thrombus formation, due to the conformational change of integrin GPIIb/IIIa from a low to a high affinity state for the plasma protein fibrinogen. This may result in fatal thrombotic events, thrombocytopenia, as well as severe bleeding complications. Therefore, thus there is a need for novel therapeutic approaches that prevent platelet-related coagulation disturbances associated with hypothermia.

Preoperative treatment with the GPIIb/IIIa blockers, tirofiban and eptifibatide, has been reported to preserve platelet function during CPB. However, a significant side effect of the currently used intravenous therapeutic strategies for GPIIb/IIIa inhibition during hypothermia is their inhibitory effect on all circulating platelets with a consecutive risk for bleeding complications. Therefore, the current intravenous GPIIb/IIIa blockers have significant limitations. Thus there is a substantial need for a safer and more efficient pharmacological approach. A single-chain antibody directed against GPIIb/IIIa that selectively blocks the activated form of the receptor only has been described. See Schwarz et al., Circ Res., 2006, 99:25-33 and Stoll et al., Arterioscler Thromb Vasc Biol., 2007, 27:1206-1212.

Short elastin-like peptides exhibit the similar temperature-induced structural transitions as elastin polymers. See Reiersen et al., J Mol. Biol., 1998, 283:255-264. Temperature-responsive elastin-like polypeptide linkers have been disclosed to modulate single-chain antibody affinity. See Megeed et al., Biomacro-molecules, 2006, 7:999-1004.

SUMMARY

This disclosure relates to temperature sensitive conjugates, compositions, and uses related thereto. In certain embodiments, the disclosure relates to conjugate polymers comprising a) a temperature sensitive polymer and b) an antibody. Typically the antibody has an epitope to a platelet receptor. The antibody may be a single-chain antibody wherein the platelet receptor is GPIIb/IIIa, such as an anti-GPIIb/IIIa antibody. In certain embodiments, the antibody binds specifically to the activated conformation of GPIIb/IIIa, i.e., an activation-specific GPIIb/IIIa antibody.

Typically, the temperature sensitive polymer is a polypeptide with repeating sequences comprising proline, such as a repeating sequence of less than 10, 9, 8, 7, 6, 5, 4, amino acids. In certain embodiments, the temperature sensitive peptide takes on a beta-sheet structure at a transition temperature of greater than about 28, 29, 30, 31, 32, 33, or 34 degrees Celsius. Typically, the temperature sensitive peptide comprises [YaaPUaaXaaZaa$_p$]$_n$ (SEQ ID NO:1) wherein Yaa is glycine, alanine, lucine, isolucine, or valine; P is proline; Uaa is glycine, alanine, lucine, isolucine, or valine; Xaa is glycine, alanine, lucine, isolucine, or valine or any amino acid except proline; Zaa is glycine, alanine, lucine, isolucine, or valine; p is 0, 1, 2, 3, 4, 5, or 6; and n is 1 to 1000. Alternatively, the temperature sensitive peptide comprises [YaaPUaaXaaZaa$_p$]$_n$ (SEQ ID NO:1) wherein Yaa is alanine or valine; P is proline; Uaa is glycine or alanine; Xaa is glycine, alanine, or valine; Zaa is glycine, alanine, or valine; p is 0, 1, or 2; n is 1 to 1000. In another alternative, the temperature sensitive peptide comprises [VPGG] (SEQ ID NO:2), [VPGVG](SEQ ID NO:3), [VPAVG](SEQ ID NO:4), and/or [APGVGV] (SEQ ID NO:5) repeat motifs. Typically, the polypeptide takes on a beta-sheet structure at a transition temperature of greater 28 degrees Celsius.

In certain embodiments, the disclosure relates to methods of preventing platelet aggregation comprising a) cooling the body temperate of a subject below 35 degrees Celsius and b) administering a conjugate polymer comprising i) an temperature sensitive polymer and ii) an antibody with an epitope to a platelet receptor. Typically the conjugate polymer is a polypeptide with repeating sequences comprising proline and the antibody is an anti-GPIIb/IIIa antibody.

In certain embodiments, the conjugate polymer is administered in combination with an antithrombotic such as a thrombolytic, anticoagulant or antiplatelet agent. Typically, the antithrombotic is aspirin, heparin, heparin sulfate, danaparoid sodium, clopidogrel, prasugrel, ticagrelor, cangrelor, elinogrel, cilostazol, abciximab, eptifibatide, tirofiban, dipyridamole, epoprostenol, abciximab, eptifibatide, tirofiban, beraprost, prostacyclin, iloprost, and treprostinil, aloxiprin, carbasalate calcium, indobufen, triflusal dipyridamole, picotamide, terutroban, triflusal cloricromen, ditazole, acenocoumarol, coumatetralyl, dicoumarol, ethyl biscoumacetate, phenprocoumon, warfarin, clorindione, diphenadione, phenindione, tioclomarol, defibrotide, ramatroban, antithrombin III, and/or protein C (drotrecogin alfa) or combinations thereof.

In certain embodiments, the disclosure relates to methods of preventing platelet aggregation comprising a) cooling the body temperate of a subject below 35 degrees Celsius, typically less than 31 or 20 degrees, and b) administering a conjugate polypeptide comprising i) a temperature sensitive peptide and ii) an antibody with an epitope to a platelet receptor.

In certain embodiments, the disclosure relates to isolated nucleic acids encoding a conjugate polypeptide comprising: a) a temperature sensitive peptide and b) an antibody with an epitope to a platelet receptor, wherein the nucleic acids are optionally operably linked to a promoter and/or a sequence that encodes a polypeptide marker.

In certain embodiments, the disclosure relates to protein expression systems comprising a nucleic acid encoding a conjugate polypeptide comprising: a) a temperature sensitive peptide and b) an antibody with an epitope to a platelet receptor.

In certain embodiments, the disclosure relates to recombinant vectors comprising a nucleic acid encoding a conjugate polypeptide comprising: a) a temperature sensitive peptide and b) an antibody with an epitope to a platelet receptor.

In certain embodiments, the disclosure relates to genetically modified microorganisms that express a conjugate polypeptide comprising: a) a temperature sensitive peptide and b) an antibody with an epitope to a platelet receptor.

In certain embodiments, the disclosure relates to methods of expressing a conjugate polypeptide comprising: a) a temperature sensitive peptide and b) an antibody with an epitope to a platelet receptor in a host cell by mixing a recombinant vector comprising a nucleic acid encoding the conjugate polypeptide and a protein expression system under conditions such that the polypeptide is formed.

BRIEF DESCRIPTION OF THE FIGURES

FIG. 4B shows data on temperature-specific binding of EMP-scFv and inhibition of fibrinogen binding to human platelets by EMP-scFv. Bar graphs and histograms represent blocking of GPIIb/IIIa at 22° C., but not at 37° C.

TERMS

Figure 1A:
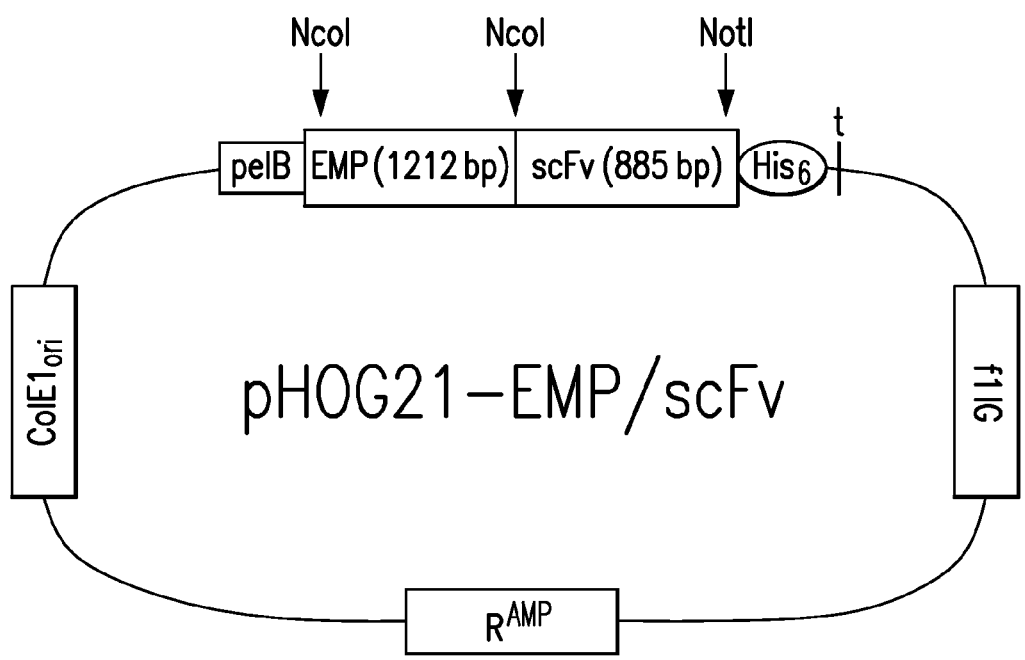
FIG. 1A shows a map of the pHOG21-EMP-scFv fusion construct, and of different elusion fractions after purification. EMP indicates the region encoding for the elastin-mimetic polypeptide; scFv indicates the region encoding for the activation-specific anti-GPIIb/IIIa scFv. RAMP indicates an ampicillin resistance gene, ColE1 ori=origin of replication of E. coli; f1IG=filamentous intergenic region; pelB=leader peptide sequence of pectate lyases pelB; His6=repeat sequence of six histidines. NcoI/NotI=restriction sites.

To facilitate understanding of embodiments of the disclosure, a number of terms are defined below.

"Antibody" refers to intact molecules as well as fragments thereof which are capable of specific binding to an epitopic determinant. Antibodies that bind a polypeptide (for example, a polypeptide encoded by a nucleic acid of the present disclosure) can be prepared using intact polypeptides or fragments as the immunizing antigen. These antigens may be conjugated to a carrier protein, if desired.

The term "chimera" when used in reference to a polypeptide refers to the expression product of two or more coding sequences obtained from different genes, that have been cloned together and that, after translation, act as a single polypeptide sequence optionally containing leading, tailing, and/or linking sequences that may be utilizes as markers, e.g., epitopes to fluorescent antibodies. Chimeric polypeptides are also referred to as "hybrid" polypeptides.

The term "expression vector" refers to a recombinant DNA molecule containing a desired coding sequence and appropriate nucleic acid sequences necessary for the expression of the operably linked coding sequence in a particular host cell. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "fusion" when used in reference to a polypeptide refers to a chimeric protein containing a protein of interest joined to an exogenous protein fragment (the fusion partner).

The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "host cell" refers to any cell capable of replicating and/or transcribing and/or translating a heterologous gene or cDNA. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The term "isolated" when used in relation to a nucleic acid refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

"Nucleic acid", as used herein, refers to a polymer of nucleotides in which the 3' position of one nucleotide sugar is linked to the 5' position of the next by a phosphodiester bridge. In a linear nucleic acid strand, one end typically has a free 5' phosphate group, the other a free 3' hydroxyl group. Nucleic acid sequences may be used herein to refer to oligonucleotides, or polynucleotides, and fragments or portions thereof, and to DNA or RNA of genomic or synthetic origin which may be single- or double-stranded, and represent the sense or antisense strand.

"Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences.

The terms "protein" and "polypeptide" refer to compounds comprising amino acids joined via peptide bonds and are used interchangeably.

"Promoter", as used herein, refers to the 5'-flanking, non-coding sequence adjacent a coding sequence which is involved in the initiation of transcription of the coding sequence.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

As used herein, "subject" refers to any animal, preferably a human patient, livestock, or domestic pet.

DETAILED DISCUSSION

Disclosed herein are certain compositions and methods useful in medically-employed hypothermia in order to prevent ischemia-induced organ damage e.g., during cardiac surgery to directly control anticoagulation, by temperature-regulated inhibition of platelet receptors such as the GPIIb/IIIa receptor.

In certain embodiments, elastin-mimetic polypeptides (EMPs) are fused to an antibody with an epitope to a platelet receptor, such as a GPIIb/IIIa-blocking single-chain antibody (scFv). In silico modelling illustrates the sterical hindrance of a β-spiral conformation of EMPs preventing the scFv from inhibiting GPIIb/IIIa at 37° C. CD spectra demonstrated reverse temperature transition, and flow cytometry showed binding to, and blocking of, GPIIb/IIIa at hypothermic (≤32° C.), but not at normal body temperature. Experiments disclosed herein show that platelet aggregation and in vivo thrombosis in mice was selectively inhibited by reducing body temperature. Therapeutic hypothermia, as used during long-term or cardiac surgery, may be made safer with fewer pro-thrombotic complications and less post-operative bleeding via direct reversal of platelet function after rewarming The fusion of an elastin-mimetic polypeptide (EMP) to an activation-specific GPIIb/IIIa-blocking single-chain antibody (scFv) enables selective hypothermia-induced anti-platelet therapy. Although it is not intended that certain embodiments of the disclosure be limited to any particular mechanism, in order to illustrate how the β-spiral conformation of EMP may prevent the scFv from inhibiting GPIIb/IIIa at 37° C., a structural model of the EMP-scFv fusion is proposed. This model indicates that the β-spiral EMP obstructs the scFv from binding to, and in turn inhibiting, GPIIb/IIIa. Below the conformational-transition temperature, i.e. 22° C., EMP is reported to adopt a random unstructured conformation. The random EMP conformation does not efficiently preclude the scFv from interacting with, and inhibiting, GPIIb/IIIa.

The EMP-anti-GPIIb/IIIa-scFv fusion protein proved to be thermally responsive, as it demonstrated significant affinity for activated platelets at 22° C., but not at 37° C. The binding of fibrinogen to activated platelets was abolished in the presence of EMP-anti-GPIIb/IIIa-scFv at 22° C., but not influenced at 37° C. EMP-scFv prevents aggregation of activated platelets at 22° C., but not when the temperature was increased to 37° C. In addition, in vivo studies further demonstrate the antithrombotic efficacy of EMP-scFv, as thrombosis in carotid arteries of mice treated with EMP-scFv was significantly prolonged at 28° C., whereas no prolongation was observed at 37° C. This indicates that EMP-driven conformational change allows for temperature-dependent binding of scFv and hypothermia-specific inhibition of activated GPIIb/IIIa receptors on platelets. This was further confirmed by demonstrating the inability of EMP alone to bind to platelets regardless of their activation state or temperature.

Mild (31-34° C.), moderate (25-30° C.) and deep hypothermia (<20° C.) are routinely employed in cardiac surgery during CPB and especially for deep hypothermic circulatory arrest (DHCA). In certain embodiments, this disclosure relates to using conjugates disclosed herein during these surgical procedure or other procedures. For example, hypothermia has also been used to lower patients' body temperature during long-lasting neurosurgical procedures and has also been successfully used to improve the recovery of patients after cardiac arrest.

In vitro and in vivo experiments have shown that hypothermic temperatures induce platelet activation and lead to a rise in microvascular thrombus formation via activation of the GPIIb/IIIa receptor and subsequent fibrinogen binding. Furthermore, studies have shown that 33-88% of patients undergoing open heart surgery suffer from some degree of postoperative neurological impairment and cognitive dysfunction. Hypothermia-induced platelet aggregation has also been shown to be closely related to cognitive decline after coronary artery bypass surgery. Neurological dysfunction after hypothermia exposure may therefore be caused by impaired perfusion of the microvasculature caused by hypothermia-induced platelet aggregates. In addition, hypothermia has been reported to cause micro-infarctions of the liver caused by sequestered platelets as well as thrombus formation in the pancreatic microcirculation leading to acute pancreatitis. Therefore, in order to inhibit platelet aggregation, preserve platelet function, and to avoid haemostatic dysfunction as well as platelet-mediated thrombosis, during hypothermia it is highly desirable to prevent hypothermia-associated platelet activation and platelet loss. At hypothermia the EMP-scFv fusion protein is a highly potent blocker of the activated form of the GPIIb/IIIa receptor. Our findings demonstrate that platelet fibrinogen binding and aggregation were significantly inhibited by the EMP-scFv at 22° C., but not at 37° C.

These temperature-dependent anti-aggregation effects of EMP-scFv are further supported by flow chamber experiments, which showed that hypothermic temperatures induced the binding of EMP-scFv to platelet aggregates under physiological flow conditions. Furthermore, once bound to activated platelets at hypothermic conditions, EMP-scFv does not dissociate from the cells following the increase in temperature. By doing so, the fusion protein prevents the exposure of the unblocked active form of GPIIb/IIIa, thus inhibiting binding of fibrinogen and thrombus formation upon rewarming. Therefore, the major advantage of the described temperature-regulated GPIIb/IIIa inhibitor is its potential to protect platelets and prevent thrombosis during clinical settings in which hypothermia is employed, but provide fully functional platelets upon rewarming of the patient.

Although it is not intended that certain embodiments of the disclosure be limited to any mechanism, it is believed that the temperature-dependent binding of EMP-scFv to activated platelets is driven by the temperature-dependent conformational change of the EMP component of the fusion protein. It is hypothesize that at lower temperatures the EMP portion of the fusion protein is in a loose, fully expanded state, referred to as a random coil. However, as the temperature is increased the EMP segment of the fusion protein collapses to form a β-sheet. This results in masking of the binding site on the anti-GPIIb/IIIa scFv, which would explain our data obtained at 37° C. where the binding of EMP-scFv to platelets, as well as its ability to inhibit fibrinogen binding and ADP-driven platelet aggregation were completely omitted. The in silico structural analysis of the EMP-scFv fusion protein supports this hypothesis. The RXD motif in the CDR3 region of the heavy chain, which constitutes the binding site of the anti-GPIIb/IIIa antibody, is embedded in β-spiral structure of the EMP and thus not accessible for binding to GPIIb/IIIa at 37° C. Therefore, this further confirms the ability of a temperature-responsive peptide, such as EMP, to exert a novel control over a scFv function during hypothermic conditions.

Although the thermal transition profile of EMP-scFv revealed the transition temperature of 28° C., the fusion protein was still capable of binding to activated platelets and significantly inhibiting the binding of fibrinogen at 32° C. This is most likely because at 32° C., the EMP-scFv has not completely adopted the β-turn structure, suggesting that the RXD motif in the CDR3 region has not been completely blocked by EMP, and is thus still capable of binding to activated form of GPIIb/IIIa. Previous studies have shown that the drop in protein concentration, as well as the properties of the accompanying fusion protein, can result in the increase of the real transition temperature. Therefore, since the concentration of EMP-scFv used in our flow cytometry experiments was at least 5 times lower than that applied in the CD studies, it is not unusual to see the binding of EMP-scFv to the activated platelets at 32° C., which is 5° C. above its transition temperature determined by a CD assay. Drug activity at this temperature broadens the potential use of the newly described temperature-controlled strategy for the increasingly widely used mild therapeutic hypothermia in order to increase the survival and improve neurological outcome in patients after out-of-hospital cardiac arrest.

The temperature-controlled GPIIb/IIIa inhibition by EMP-scFv was also demonstrated in vivo. At hypothermia EMP-scFv revealed a strong anti-thrombotic effect in the mouse carotid artery. The limited clinical data available, suggest that pharmacological platelet inhibition during coronary artery bypass grafting (CABG) with aspirin or clopidogrel protects patients from ischemic events. Furthermore, administration of GPIIb/IIIa blockers, such as eptifibatide and tirofiban, in the preoperative period of CABG has been reported to decrease the incidence of perioperative myocardial infarction and platelet loss as well as the need for minor transfusions during CABG. Also, biochemical markers show less activation of the haemostatic and inflammatory system. However, despite these initial promising reports about the effects of GPIIb/IIIa blockers during cardiac surgery, the currently available agents, particularly abciximab, are too long-acting to provide controllable platelet inhibition that is restricted to the time period of the actual surgical intervention and thus are feared to result in bleeding complications after the surgical procedure. Overall, due to the dichotomy of anti-thrombotic (anti-ischemic) and anti-haemostatic effects of the currently clinically available anti-platelet drugs, strong evidence for the overall benefit of platelet inhibition in CABG has not been demonstrated. However, reversible anti-platelet compounds disclosed herein represent an ideal approach for platelet protection in patients undergoing CABG. Moreover, unlike commercially approved GPIIb/IIIa blockers such as abciximab and eptifibatide, which in addition to blocking platelets have also been shown to antagonize ligand binding to $\alpha_v/\beta_3$ integrins on vascular cells, studies in our laboratory demonstrated that our scFv is GPIIb/IIIa-specific and binds to activated platelets exclusively.

Ligand-mimetic GPIIb/IIIa blockers might be associated with paradoxical platelet activating effects. However, activation-specific blockade of GPIIb/IIIa using scFv has been shown to have a substantial advantage in regards to bleeding risks, as it does not prolong bleeding time in contrast to the currently clinically used conformation unspecific GPIIb/IIIa inhibitors. Moreover, unlike commercially approved GPIIb/IIIa blockers such as abciximab and eptifibatide, which in addition to blocking platelets have also been shown to antagonize ligand binding to $\alpha v/\beta 3$ integrins on vascular cells, studies demonstrated that our scFv is GPIIb/IIIa-specific and binds to activated platelets exclusively. Therefore, it is reasonable to hypothesize that activation-specific scFv would not bind to all circulating platelets, but only to those expressing the active form of GPIIb/IIIa receptor during hypothermia, and thus facilitate the establishment of proper homeostasis upon rewarming. In the current study, in vivo evaluation of temperature-regulated EMP-scFv revealed an anti-thrombotic effect of the fusion protein, which is comparable to the clinically used GPIIb/IIIa blocker eptifibatide, at 28° C. but not at 37° C. Furthermore, the observation that EMP-scFv exhibited significant anti-thrombotic effects in our jugular vein model under hypothermic conditions, suggests that this strategy could prove beneficial in relation to a prophylactic approach during surgery in preventing venous thrombosis and pulmonary embolism. Overall, the administration of a temperature-dependent and activation-specific GPIIb/IIIa receptor blocker developed in this study is a highly attractive concept, due to the potential of this approach to achieve an unprecedented optimal therapeutic control of platelet function during and after hypothermia.

Coagulation Mechanisms and Related Antibodies

With certain embodiments, it is contemplated that temperature sensitive polymers may be conjugated to any antibodies that bind peptides involved in the coagulation biological pathway and utilized in manners disclosed herein. The antibodies may be obtained by generating peptide fragments of target molecules as antigens using known methods some of which are described herein.

Integrins are adhesion receptors that mediate vital bidirectional signals during morphogenesis, tissue remodeling, and repair. These glycoproteins functions as a specific receptor for adhesive proteins and interacts with its ligand via the recognition of short amino acid sequences, including the motif Arg-Gly-Asp (RGD). Integrins are abundantly expressed on the platelet surface. When platelet activation is initiated, a conformational change in integrins to a high-affinity state (activated) for the plasma protein fibrinogen results in platelet aggregation followed by thrombus formation.

GPIIb/IIIa (glycoprotein IIb of IIb/IIIa complex) is also known as antigen CD41 and integrin alpha chain 2b ($\alpha_{IIb}\beta_3$). Alpha chain 2b undergoes post-translational cleavage to yield disulfide-linked light and heavy chains that join with beta 3 to form a fibronectin receptor expressed in platelets that plays an important role in coagulation. The RGD peptide binds to GPIIIa an domain that contains the sequence from residue 109 to residue 171. Andrieux et al. J Bio Chem., 1991, 266 (22):14202-14207, hereby incorporated by reference, disclose a method of generation anti-GPIIb/IIIa antibodies using synthetic peptides corresponding to sequences contained within the RGD-binding region, e.g., DYPVDIYYLMDL-SYSMKDDL (SEQ ID NO:22), of GPIIIa as antigens. Certain of these antibodies interact only with stimulated platelets, inhibit fibrogen binding, and platelet aggregation, i.e., activation specific.

Single-chain antibodies (scFvs), typically consist of the variable regions of the heavy and light chain of the antibody, connected by a linker peptide. Schwarz et al., Circ Res., 2006, 99:25-33 and Schwarz et al., FASEB J. 2004; 18: 1704-1706, hereby incorporated by reference, disclose methods of generating single-chain anti-GPIIb/IIIa antibodies that are activation specific.

In certain embodiments, it is contemplated that conjugates may be produced with antibodies to other proteins that manage coagulant activity or are involved in coagulation such as antibodies to other platelet receptors and ligands. Collagen supports platelet adhesion through direct and indirect pathways and directly activates the cells initiating aggregation and coagulant activity. Platelet adhesion and aggregation on collagen is an integrated process that involves several platelet agonists that act through a variety of surface receptors including e.g., integrins. For example, the platelet integin glycoprotein Ib-V-IX (GPIb-V-IX) and von Willebrand factor (VWF) immobilized on collagen is important for the initial tethering (or capture) of flowing platelets. Collagen activates platelets through collagen receptors glycoprotein VI (GPVI) and integrin $\alpha 2\beta 1$ and induces platelet plug formation and occlusion at sites of vessel damage by recruiting platelets to exposed collagen. Inoue et al., J Bio Chem., 2008, 283, 16279-16282, hereby incorporated by reference, disclose antibodies (anti-VWP antibodies) that block associations between GPIb-IX-V and von Willebrand factor (VWF) inhibit platelets adhere to laminin. Laminin induces platelet activation that leads to cell spreading. Laminin stimulates platelets by binding to the collagen receptor GPVI, and this interaction is facilitated by integrin $\alpha 6\beta 1$. See Inoue et al., J Bio Chem., 2008, 283, 16279-16282. In certain embodiments, the disclosure relates to conjugate polypeptides comprising a) a temperature sensitive peptide and b) an antibody with an epitope to a GPIb-V-IX, GPVI, VWF, or laminin or fragments thereof.

Thrombin and adenosine diphosphate (ADP) are platelet activators. Thrombin triggers human platelet activation via protease-activated receptors (PARs), PAR1 and PAR4. ADP is secreted by platelets in response to multiple extracellular signals, including thrombin acting via PARs. Secreted ADP acts in an autocrine/paracrine fashion on the platelet ADP receptor P2RY12 (purinergic receptor P2Y G protein-coupled 12) to amplify and sustain platelet activation. In certain embodiments, the disclosure relates to conjugate polypeptides comprising a) a temperature sensitive peptide and b) an antibody with an epitope to thromibin, PAR1, PAR 4, or P2RY12 or fragments thereof.

The antibodies can be produced by immunizing an animal such as, but not limited to, a rabbit or a mouse, with a protein, or a portion thereof, or by immunizing an animal using a protein comprising at least a portion of the polypeptide. One skilled in the art would appreciate, based upon the disclosure provided herein, smaller fragments of these proteins can also be used to produce antibodies that specifically bind the polypeptide.

Certain embodiments of the disclosure encompass polyclonal, monoclonal, synthetic antibodies, and the like. Moreover, the antibody can be used to detect and or measure the amount of protein present in a biological sample using well-known methods such as, but not limited to, Western blotting and enzyme-linked immunosorbent assay (ELISA). The antibody can also be used to immunoprecipitate and/or immuno-affinity purify their cognate antigen using methods well-known in the art.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See, e.g., U.S. Pat. Nos. 4,816,567 and 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. Nos. 7,125,689 and 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Temperature Sensitive Polymers

As used herein, the terms "temperature sensitive polymer" refer to a polymer that undergoes conformational stability changes within physiologically relevant temperatures, e.g., between 5 to 40 degrees Celsius. Conformational instability generally increases the elasticity of a polymer; however, a conformationally stable polymer typically has relatively less elasticity. The change may occur dramatically near a certain temperature or gradually over a temperature range. An "elastic temperature sensitive polymer" refers to a temperature sensitive polymer with elastin or elastin-like repeating units as described herein within the polypeptide, e.g., the temperature sensitive peptide comprises [VPGG] (SEQ ID NO:2), [VPGVG](SEQ ID NO:3), [VPAVG](SEQ ID NO:4), and/or [APGVGV] (SEQ ID NO:5) repeat motifs.

Any variety of proteins may be modified in order to provide desired conformational stability changes at physiologically relevant temperatures. Improving beta-turns by substituting proline residues is a generally useful way of increasing protein stability. Trevino et al., J Mol. Biol., 2007, 373(1):211-218, disclose that the following guidelines are useful when attempting to increase protein stability by mutating non-proline and non-glycine residues to preferred proline or preferred glycine. 1) The wild-type residue should not be involved in stabilizing interactions such as hydrogen bonds or favorable electrostatic interactions. Also, since proline lacks an amide hydrogen, mutations to proline should be avoided at positions where the amide nitrogen is a hydrogen bond donor. 2) Bulky hydrophobic or aromatic residues such as Val, Leu, Ile, Phe, Tyr, and Trp should not be targeted as they might be partially buried and provide favorable hydrophobic interactions. 3) Mutations to proline near in sequence to Cys residues involved in disulfide bonds should be avoided. 4) Asparagine residues in the i+1 position of type I' β-turns should not be targeted as they are highly preferred in these positions. 5) Mutations in type IV or type VIII turns are less desirable as these turns are more often buried than other β-turn types.

In certain embodiments, the disclosure relates to conjugate polymers comprising a temperature sensitive polymer that changes structural form at or below normal mammalian physiological temperatures. Elastin-like polypeptides exhibit the similar temperature-induced structural transitions as elastin polymers in the formation of a beta-spiral structure. See Reiersen et al., J Mol. Biol., 1998, 283:255-264. Within certain embodiments, it is contemplated that the temperature sensitive polypeptide forms beta spiral structures or an alpha helix or other secondary form. In certain embodiments, the temperature sensitive polymers comprises peptides characterized by an inverse temperature transition, i.e., wherein the largely unstructured elastin repeats gain β-sheet structure at temperatures greater than the transition temperature Megeed et al., Biomacromolecules, 2006, 7(4):999-1004, hereby incorporated by reference, disclose that a single-chain antibody with a temperature-responsive elastin like linker. Single-chain antibodies containing elastin-like polypeptide linkers have equilibrium affinity comparable to wild-type at room temperature but altered binding kinetics as the temperature is raised.

In certain embodiments, the temperature sensitive peptide takes on an alternative secondary structure at a transition temperature of greater than about 28, 29, 30, 31, 32, 33, 34 degrees Celsius. Typically, the temperature sensitive peptide comprises [YaaPUaaXaaZaa$_p$]$_n$ (SEQ ID NO:1) wherein is Yaa glycine, alanine, lucine, isolucine, or valine; P is proline; Uaa is glycine, alanine, lucine, isolucine, or valine; Xaa is any amino acid except proline, Xaa is valine or histidine, or Xaa is glycine, alanine, lucine, isolucine, or valine; Zaa is glycine, alanine, lucine, isolucine, or valine; p is 0, 1, 2, 3, 4, 5, or 6; and n is 1 to 1000. Alternatively, the temperature sensitive peptide comprises [YaaPUaaXaaZaa$_p$]$_n$ (SEQ ID NO:1) wherein is Yaa alanine or valine; P is proline; Uaa is glycine or alanine; Xaa is glycine, alanine, or valine; Zaa is glycine, alanine, or valine; p is 0, 1, or 2; n is 1 to 1000. In another alternative, the temperature sensitive peptide comprises [VPGG] (SEQ ID NO:2), [VPGVG](SEQ ID NO:3), [VPAVG](SEQ ID NO:4), and/or [APGVGV] (SEQ ID NO:5) repeat motifs.

Meyer et al., Cancer Res, 2001, 61:1548—disclose elastin-like polypeptides comprising Val-Pro-Gly-Xaa-Gly. In certain embodiments, the disclosure relates to a conjugate polypeptide with an elastic temperature sensitive polypeptide comprising Val-Pro-Gly-Xaa-Gly (SEQ ID NO: 19), Val-Pro-Ala-Xaa-Gly (SEQ ID NO: 20), or Ala-Pro-Gly-Xaa-Gly (SEQ ID NO: 21) where the "guest residue" Xaa can be any amino acid except Pro or Xaa is valine or histidine. The amino acid sequences of tryptic fragments of aortic tropoelastin were disclosed in Sandberg et al., Pathol Biol, 1985, 33(4): 266-74. In certain embodiments, the disclosure relates to an elastic temperature sensitive peptide comprising repeating polypeptides comprising GVP (SEQ ID NO:14), GGVP (SEQ ID NO:15), PGVGV (SEQ ID NO:15), PGVGVA (SEQ ID NO:17), and AGVPGFGVG (SEQ ID NO:18).

Within certain embodiments, it is contemplated that the temperature sensitive polymer is a block copolymer hydrogel such as poly(N-substituted acrylamide)-based block copolymer hydrogels, poly(vinyl ether)-based block copolymer hydrogel or a PEO/PPO-based block copolymer hydrogel. He et al., J Controlled Release, 2008, 127:189-207, hereby incorporated by reference, disclose certain block copolymer hydrogel and their preparation.

Any of the temperature sensitive polymers may be conjugated to antibodies disclosed herein by well-known coupling methods, amid coupling methods, such as by transforming a carboxylic acid on the temperature sensitive polymer, e.g., incorporating terminal or transient vinyl with a carboxylic acid group, to an activated intermediate using typical peptide coupling reagents, and reacting the temperature sensitive polymer with a free amine or thiol group incorporated in the antibody, e.g., incorporating a terminal lysine or cysteine amino acid.

A variety of temperature sensitive polymers are described below. In certain embodiments, it is contemplated that the temperature sensitive polymer comprises poly(N-isopropylacrylamide) (PNIPAM), poly(N,N-diethylacrylamide) (PDEAM), poly(vinyl ether) (PVE), poly(N-vinylalkylamide (PNVAAM), poly(N-vinylcaprolactam) (PNVCa), polyphosphazene derivatives, and/or poly(N-(2-hydroxypropyl) methacrylamide mono/dilactate) (PHPMAM-mono/dilactate).

In certain embodiments, the temperature sensitive polymer comprises AB, BAB, A(B)$_4$, and A(B)$_8$ linear and star-shaped block copolymers with poly(ethylene glycol) (PEG) as the A block and any polymer disclosed herein as the B block. In one embodiment, the temperature sensitive polymer comprises a ABA triblock copolymers with PNIPAM as the A block and poly(-methacryloyloxyethyl phosphorylcholine) (PMPC) as the central B block. In another embodiment, the temperature sensitive polymer comprises ABC-type poly(propylene oxide)-PMPC-PNIPAM triblock copolymers (PPO-PMPC-PNIPAM). In another embodiment, the temperature sensitive polymer comprises a poly(-(2-ethoxy)ethoxyethyl vinyl ether)-poly(-methoxyethyl vinyl ether) (PEOEOVE-PMOVE) diblock copolymer. In another embodiment, the temperature sensitive polymer comprises a poly(-ethoxyethyl vinyl ether)-poly(-hydroxyethyl vinyl ether) diblock copolymer (PEOVE-PHOVE), a poly(-hydroxybutyl vinyl ether)-PHOVE diblock copolymer (PHOBVE-PHOVE), or PMOVE-poly(octadecyl vinyl ether) (PMOVE-PODVE) diblock and random copolymers. In another embodiment, the temperature sensitive polymer comprises poly(ethylene oxide)-b-poly(propylene oxide)-b-poly(ethylene oxide) triblock copolymers (PEO-PPO-PEO), PEO-poly(1,2-butylene oxide)-PEO triblock copolymers (PEO-PBO-PEO).

In certain embodiments, the temperature sensitive polymer comprises poly(D,L-lactide) (PLA) or poly(8-caprolactone) (PCL), In certain embodiments, the temperature sensitive polymer comprises ABA type PEG-poly(L-lactide)-PEG triblock copolymers (PEG-PLLA-PEG), PEG-poly(trimethylene carbonate) (PEG-PTMC) diblock copolymers, PEG-poly (trimethylene carbonate) (PEG-PTMC) diblock copolymers.

Combination Therapies

In some embodiments, the disclosure relates to compositions and methods of administering to a subject conjugates disclosed herein in combination with other antithrombotics (thrombolytics, anticoagulants and antiplatelet drugs) such as aspirin, heparin, heparin sulfate, or danaparoid sodium. As used herein, the term "combination with" when used to describe administration with an additional treatment means that the agent may be administered prior to, together with, or after the additional treatment, or a combination thereof.

In certain embodiments, the antiplatelet drugs are glycoprotein IIb/IIIa inhibitor such as abciximab, eptifibatide, and tirofiban; ADP receptor/P2Y12 inhibitors such as thienopyridines (clopidogrel, prasugrel, ticlopidine) and ticagrelor; prostaglandin analogues (PGI2) such as beraprost, prostacyclin, iloprost, and treprostinil; COX inhibitors such as acetylsalicylic acid/aspirin, aloxiprin, carbasalate calcium, indobufen, and triflusal; thromboxane synthase inhibitors such as dipyridamole, picotamide; receptor antagonist such as terutroban; phosphodiesterase inhibitors such as cilostazol, dipyridamole, triflusal or others such as cloricromen and ditazole.

In certain embodiments, the antithrombotics are vitamin K antagonists such as coumarins: acenocoumarol, coumatetralyl, dicoumarol, ethyl biscoumacetate, phenprocoumon and warfarin; 1,3-indandiones such as clorindione, diphenadione, and phenindione or others such as tioclomarol.

In certain embodiments, the antithrombotics are defibrotide, ramatroban, antithrombin III, protein C (drotrecogin alfa).

In certain embodiments, the antithrombotics are thrombolytic drugs and/or fibrinolytics plasminogen activators such as r-tPA (alteplase, reteplase, tenecteplase), UPA (urokinase, saruplase), streptokinase, anistreplase, and monteplase.

In certain embodiments, the antithrombotics are other serine endopeptidases such as ancrod and fibrinolysin or others such as brinase.

Recombinant Protein Expression Systems

Protein expression systems refer to a combination of an expression vector, nucleic acid encoding a polypeptide, and an environment for the vector that provides a context to allow transcription of an encoded protein. For example, common protein expression systems are bacteria (such as E. coli, B. subtilis), yeast (such as S. cerevisiae) or eukaryotic cell lines. Common nucleic acid sources and delivery mechanisms are viruses (such as baculovirus, retrovirus, adenovirus), plasmids, artificial chromosomes and bacteriophage (such as lambda). Cell-free expression of proteins is possible using purified RNA polymerase, ribosomes, tRNA and ribonucleotides.

In certain embodiments, the disclosure relates to isolated nucleic acids encoding a conjugate polypeptide comprising: a) a temperature sensitive peptide and b) an antibody with an epitope to a platelet receptor for the purpose of recombinant expression. The nucleic acid may optionally contain a promoter. The nucleic acid may be complementary DNA (cDNA), i.e., DNA that has no introns. Promoters contain specific DNA sequences and response elements which provide an initial binding site for RNA polymerase and for proteins called transcription factors that recruit RNA polymerase.

There are a number of systems known to one skilled in the art for the expression of recombinant proteins. Typical expression systems include, but are not limited to, prokaryotic (bacterial) or eukaryotic (usually yeast or mammalian cell) system. Typically, a vector comprising a nucleic acid encoding the protein is incorporated with cDNA comprising a desired promoter which function in for example E. coli, yeast, or mammalian systems. In certain embodiments, the disclosure relates to a cDNA comprising a promoter and a nucleic acid encoding a conjugate polypeptide comprising: a) a temperature sensitive peptide and b) an antibody with an epitope to a platelet receptor.

In certain embodiments, the disclosure relates prokaryotic recombinant protein expression systems, including bacterial systems, comprising a nucleic acid comprising a promoter and a nucleic acid encoding a conjugate polypeptide comprising: a) a temperature sensitive peptide and b) an antibody with an epitope to a platelet receptor. For example, expression can be induced in bacterial protein expression systems comprising a lac operon promoter. Isopropyl β-D-1-thiogalactopyranoside (IPTG) triggers transcription of the lac operon. There are many commercial kits available for recombinant protein expression using prokaryotic expression systems.

In certain embodiments, the disclosure relates to eukaryotic expression systems, including yeast, mammalian cells, baculovirus cells (insect), comprising a nucleic acid with a promoter and nucleic acid encoding a conjugate polypeptide comprising: a) a temperature sensitive peptide and b) an antibody with an epitope to a platelet receptor.

The nucleic acids may be contained within expression vectors. Thus, for example, a nucleic acid sequence may be included in any one of a variety of expression vectors for expressing a polypeptide, and more than one nucleic acid of interest may be included in one expression vector. Alternatively, parts of one gene or nucleic acid may be included in separate vectors. In some embodiments of the present disclosure, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host cells.

In some embodiments of the present disclosure, the constructs comprise a vector, such as a plasmid or viral vector, into which a desired nucleic acid sequence has been inserted, in a forward or reverse orientation. The desired nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: pcDNA3.1, pCMV.5, pZEM3, pSI, pCMV.Neo and pTetOn. Any other plasmid or vector may be used as long as it is replicable and viable in the host cells. In some preferred embodiments of the present disclosure, the expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present disclosure, the nucleic acid sequence in the expression vector is operatively linked to an appropriate expression control sequence(s) (promoter) to direct mRNA synthesis. A wide variety of promoters can be used, depending on the cell type which will be used. Promoters can be constitutive, inducible, or transactivated. Promoters useful in the present disclosure include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. The following promoters have proved are contemplated: the human CMV promoter, the Rous Sarcoma Viral LTR promoter, the SV40 late promoter, the human enkephalin promoter, the human chorionic gonadotropin promoter, the mammalian tetracycline inducible promoter and several synthetic promoters. Additional promoters include CRE-CAT and ENK72 promoters.

In other embodiments of the present disclosure, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present disclosure, transcription of the nucleic acid of interest by higher eukaryotes is increased by inserting an enhancer sequence into the vector. Enhancers are cis-acting elements of DNA, usually about from 10 to 300 bp that act on a promoter to increase its transcription. Enhancers useful in the present disclosure include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present disclosure, the vector may also include appropriate sequences for amplifying expression.

Cell transfection, or the introduction of foreign nucleic acid into a cell, can be accomplished chemically, biologically, or mechanically. Current methods include use of a virus vector, lipofection, gene guns, electroporation, and microinjection.

Viral vectors commonly used for in vivo or ex vivo targeting and therapy procedures are, for example, DNA-based vectors and retroviral vectors. Methods for constructing and using viral vectors are known in the art. Typically, the viral vectors are replication defective, that is, they are unable to replicate autonomously in the target cell. In general, the genome of the replication defective viral vectors that are used within the scope of the present disclosure lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Typically, the replication defective virus retains the sequences of its genome that are necessary for encapsidating the viral particles. DNA viral vectors include attenuated or defective DNA viruses, including, but not limited to, herpes simplex virus (HSV), papillomavirus, Epstein Barr virus (EBV), adenovirus, adeno-associated virus (AAV), and the like. Defective viruses, which entirely or almost entirely lack viral genes, are typical, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector, defective herpes virus vector lacking a glycoprotein L gene, or other defective herpes virus vectors; an attenuated adenovirus vector, such as the vector described by Stratford-Perricaudet et al., J. Clin. Invest., 90:626-630 [1992]; See also, La Salle et al., Science 259:988-990 [1993].

In a certain embodiment, the vector is an adenovirus vector. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2 or type 5 human adenoviruses (AAV2 or AAV5), or adenoviruses of animal origin. Those adenoviruses of animal origin that can be used within the scope of the present disclosure include adenoviruses of canine, bovine, murine, ovine, porcine, avian, and simian (e.g., SAV) origin.

Typically, the replication defective adenoviral vectors comprise the inverted terminal repeat (ITR)s, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (Hinfll-Sau3A fragment). Other regions may also be modified, in particular the E3 region, the E2 region, the E4 region, or in any of the late genes L1-L5.

The replication defective recombinant adenoviruses according to the disclosure can be prepared by any technique known to the person skilled in the art. In particular, they can be prepared by homologous recombination between an adenovirus and a plasmid, which carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (See e.g., U.S. Pat. Nos. 4,797,368; 5,139,941). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263). The retroviruses are integrating viruses that infect dividing cells. The retrovirus genome includes two long terminal repeats (LTRs), an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus.

Typical vectors for practicing embodiments of the disclosure are lentiviral vectors. An RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Moreover, a RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), and a caprine arthritis-encephalitis virus (CAEV).

A typical lentiviral vector is one derived from HIV, most preferably HI-1, HIV-2, or chimeric combinations thereof. Of course different serotypes of retroviruses, especially HIV, may be used singly or in any combination to prepare vectors for use in the present disclosure. A "basic" lentiviral vector contains minimally, LTRs and packaging sequences in the 5' leader and gag encoding sequences, but can also optionally contain the RRE element to facilitate nuclear export of vector RNA in a Rev dependent manner. A preferred vector additionally contains nucleotide sequences that enhance the efficiency of transduction into cells.

Additional examples of lentiviral vector constructs that may be used in the present disclosure are found in U.S. Pat. Nos. 5,885,806, 5,994,136, 6,498,033, 6,835,568, 6,790,641, 6,863,884, and 7,250,299. The constructs are merely examples that do not limit the scope of vectors that efficiently transduce cells. Instead, the constructs provide additional guidance to the skilled artisan that a viral vector for use with the present disclosure may contain minimal sequences from the wild-type virus or contain sequences up to almost the entire genome of wild-type virus, yet exclude an essential nucleic acid sequence required for replication and/or production of disease. Methods for determining precisely the sequences required for efficient transduction of cells are routine and well known in the art. For example, a systematic incorporation of viral sequences back into a "basic" vector or deleting sequences from vectors that contain virtually the entire HIV genome is routine and well known in the art.

Furthermore, placing sequences from other viral backbones into viral vectors of interest, such as the cytomegalovirus (CMV), is also well known in the art. Regardless of the actual viral vector used, various accessory proteins encoded by, and sequences present in, the viral genetic material may be left in the vector or helper genomes if these proteins or sequences increase transduction efficiency in certain cell types. Numerous routine screens are available to determine whether certain genetic material increases transduction efficiency by incorporating the sequence in either the vector or helper genomes.

The viral vectors used in the present disclosure may also result from "pseudotype" formation, where co-infection of a cell by different viruses produces progeny virions containing the genome of one virus encapsulated within an outer layer containing one or more envelope protein of another virus. This phenomenon has been used to package viral vectors of interest in a "pseudotyped" virion by co-transfecting or co-infecting a packaging cell with both the viral vector of interest and genetic material encoding at least one envelope protein of another virus or a cell surface molecule. See U.S. Pat. No. 5,512,421. Such mixed viruses can be neutralized by anti-sera against the one or more heterologous envelope proteins used. One virus commonly used in pseudotype formation is the vesicular stomatitis virus (VSV), which is a rhabdovirus. The use of pseudotyping broadens the host cell range of the virus by including elements of the viral entry mechanism of the heterologous virus used.

Pseudotyping of viral vectors and VSV results in viral particles containing the viral vector nucleic acid encapsulated in a nucleocapsid which is surrounded by a membrane containing the VSV G protein. The nucleocapsid preferably contains proteins normally associated with the viral vector. The surrounding VSV G protein containing membrane forms part of the viral particle upon its egress from the cell used to package the viral vector. Examples of packaging cells are described in U.S. Pat. No. 5,739,018. In a preferred embodiment of the disclosure, the viral particle is derived from HIV and pseudotyped with VSV G protein. Pseudotyped viral particles containing the VSV G protein can infect a diverse array of cell types with higher efficiency than amphotropic viral vectors. The range of host cells include both mammalian and non-mammalian species, such as humans, rodents, fish, amphibians and insects.

The viral vector for use in the transduction methods of the disclosure can also comprise and express one or more nucleic acid sequences under the control of a promoter present in the virus or under the control of a heterologous promoter introduced into the vector. The promoters may further contain insulatory elements, such as erythroid DNAse hypersensitive sites, so as to flank the operon for tightly controlled gene expression. Preferred promoters include the HIV-LTR, CMV promoter, PGK, U1, EBER transcriptional units from Epstein Barr Virus, tRNA, U6 and U7. Pol III promoters may also be used. Tissue specific promoters are also preferred embodiments. For example, the beta globin Locus Control Region enhancer and the alpha & beta globin promoters can provide tissue specific expression in erythrocytes and erythroid cells. Another further preferred embodiment is to use cis-acting sequences that are associated with the promoters. For example, The U1 gene may be used to enhance antisense gene expression where non-promoter sequences are used to target the antisense or ribozymes molecule to a target spliced RNA as set out in U.S. Pat. No. 5,814,500.

Any cis acting nucleotide sequences from a virus may be incorporated into the viral vectors of the disclosure. In particular, cis-acting sequences found in retroviral genomes are preferred. For example, cis-acting nucleotide sequence derived from the gag, pol, env, vif, vpr, vpu, tat or rev genes may be incorporated into the viral vectors of the disclosure to further increase tranduction efficiency. Preferably, a cis acting sequence does not encode an expressed polypeptide; is not expressed as a polypeptide or part thereof due to genetic alteration, such as deletion of a translational start site; encodes only a portion or fragment of a larger polypeptide; or is a mutant sequence containing one or more substitutions, additions, or deletions from the native sequence. An example of a cis acting sequence is the cPPT (central polypurine tract) sequence identified within the HIV pol gene.

EXPERIMENTAL

Example 1

Construction, Expression and Purification of EMP-scFv

Figure 1B:
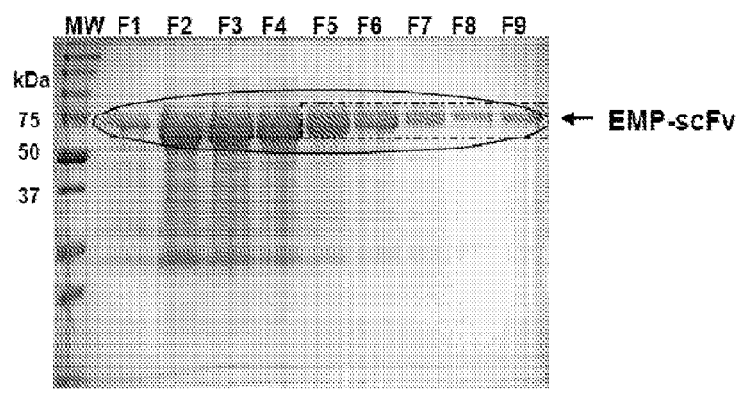
FIG. 1B shows an SDS-PAGE of number of fractions eluted (EMP-scFv is circled), but only those with the least amount of contaminating proteins were used for further in vitro and in vivo studies (dashed line). MW indicates molecular weight marker.
Figure 1C:
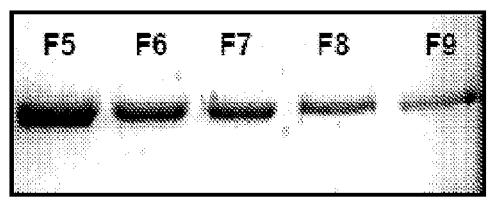
FIG. 1C shows a Western Blot detecting EMP-scFv protein in different fractions after purification, using HRP-labelled anti-His(6)-antibody.

Cloning an elastin mimetic polypeptide (EMP) cDNA upstream of the single-chain antibody (scFv) in pHOG-21 bacterial expression vector resulted in a 2115 bp fusion construct (EMP-scFv), encoding a protein consisting of 704 amino acids (FIG. 1a), with a molecular weight of approximately 70 kDa (FIG. 1b). Western Blotting using an HRP-coupled anti-His(6)-tag mAb resulted in the detection of a single band, further confirming that the protein visualized by SDS-PAGE was EMP-scFv (FIG. 1c).

Example 2

Figure 2A:
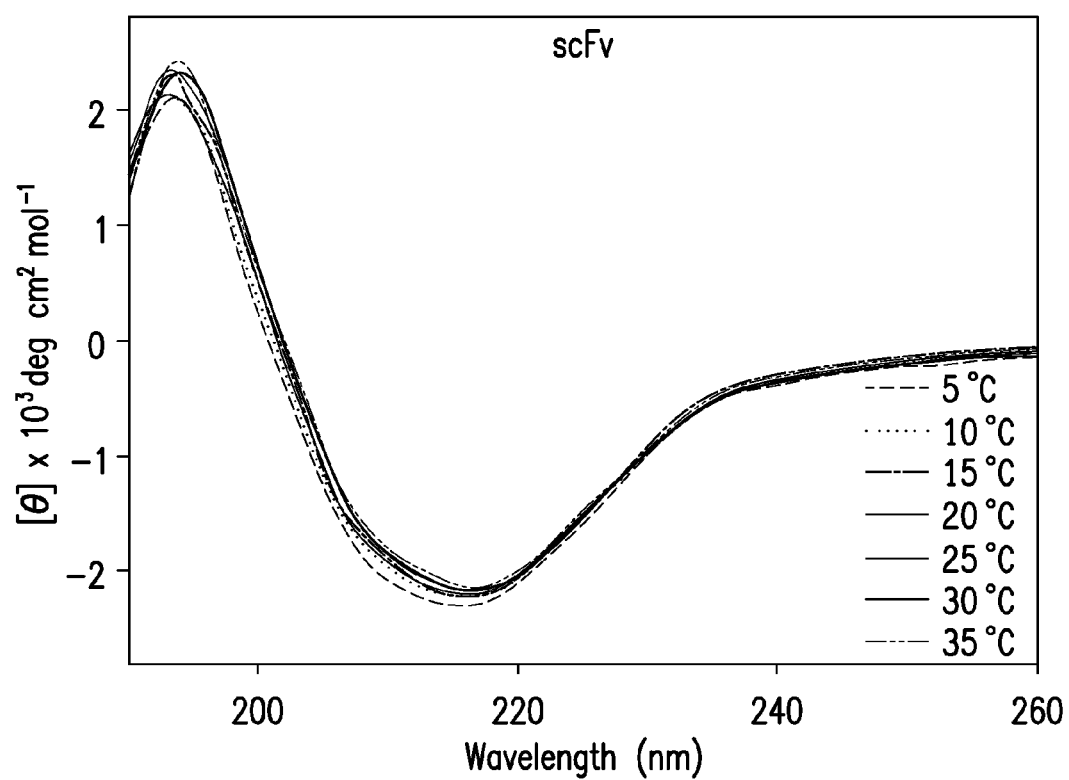
FIG. 2A shows a CD spectra and thermal transition profiles of recombinant constructs for scFv.
Figure 2B:
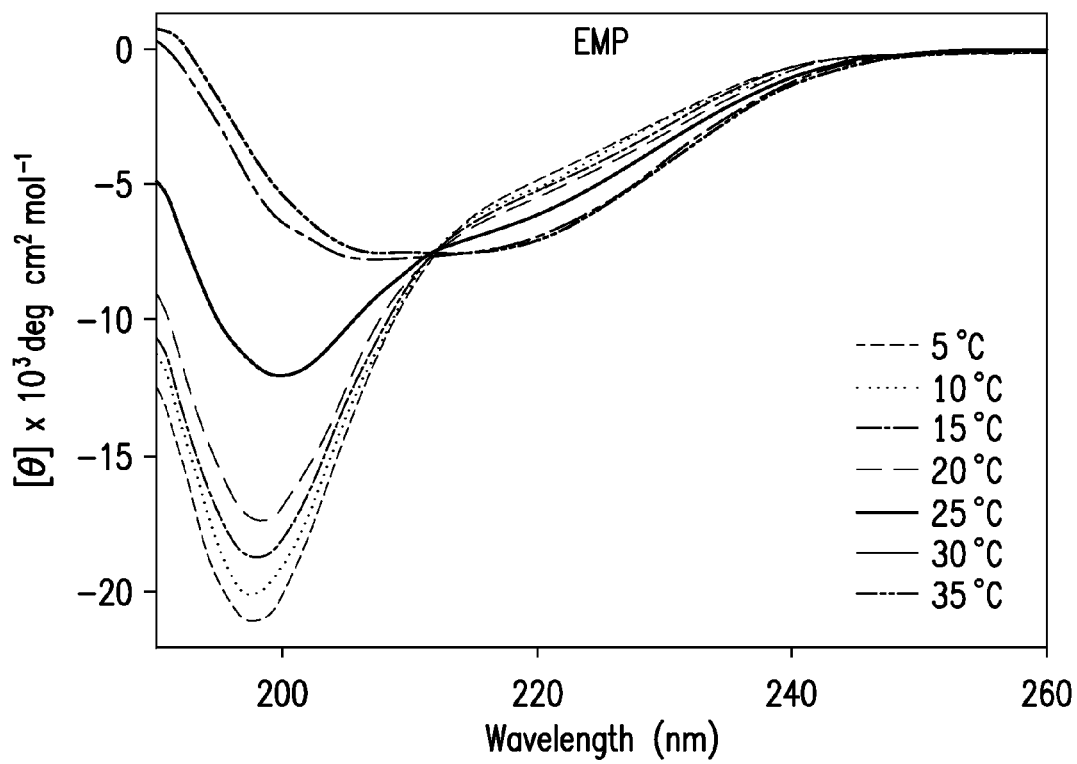
FIG. 2B shows a CD spectra and thermal transition profiles of recombinant constructs for EMP.
Figure 2C:
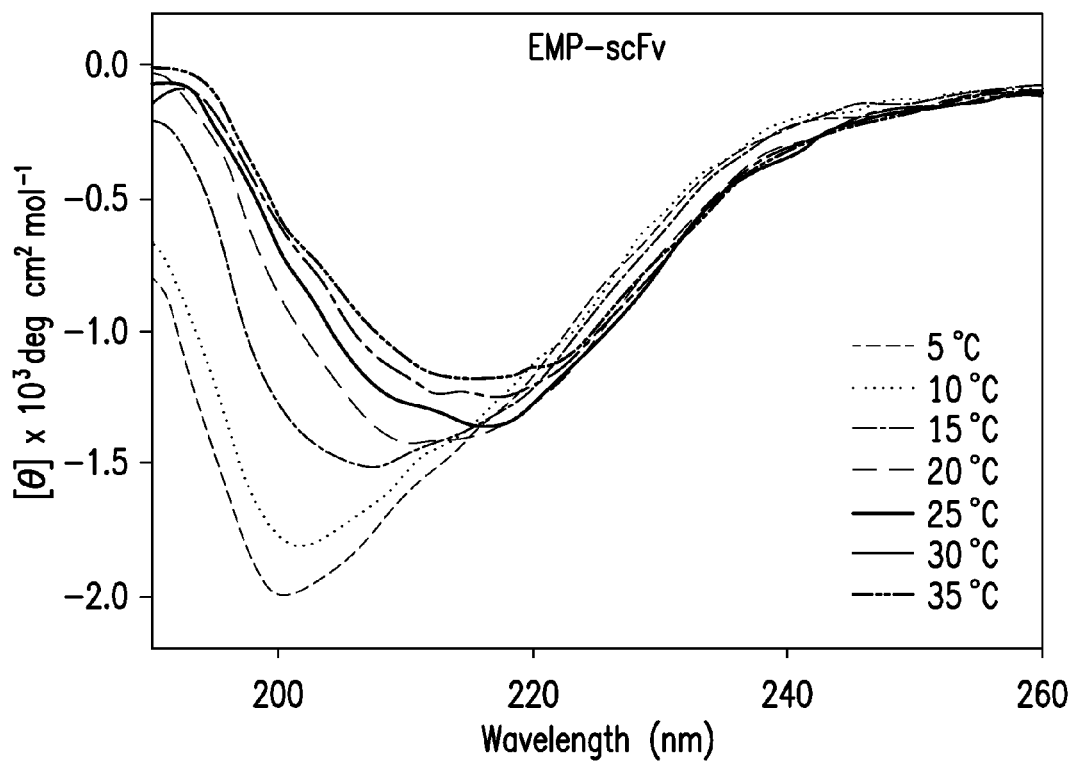
FIG. 2C shows a CD spectra and thermal transition profiles of recombinant constructs for EMP-scFv constructs.

Circular Dichroism (CD) Spectra Profiles and Thermal Transition Profiles of Recombinant Constructs The structural feature of the scFv is a β-sheet. No significant conformational changes were observed in CD as the temperature increased up to 35° C. (FIG. 2a). The EMP displayed temperature-dependent conformational rearrangement from the random coil conformation (negative ellipticity near 198 nm) to the β-turn signature (negative ellipticity near 220 nm) (FIG. 2b). Likewise, significant conformational changes can be detected in the CD spectra of EMP-scFv fusion molecule in that the random coil (negative ellipticity near 200 nm) is rapidly replaced with the putative β-turn signature (negative ellipticity near 220 nm) as the temperature approaches the transition point (FIG. 2c). The negative minimum ellipticity of the fusion protein at high temperature was slightly shifted from that of EMP indicating an interaction between two components of the fusion protein.

Figure 2D:
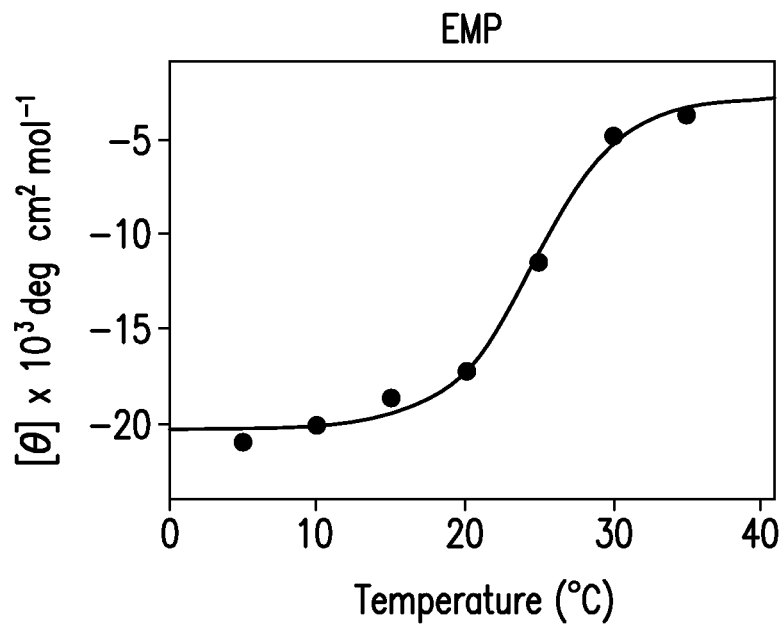
FIG. 2D shows data on the transition profiles monitoring the disappearance of the random coil structure of EMP.
Figure 2E:
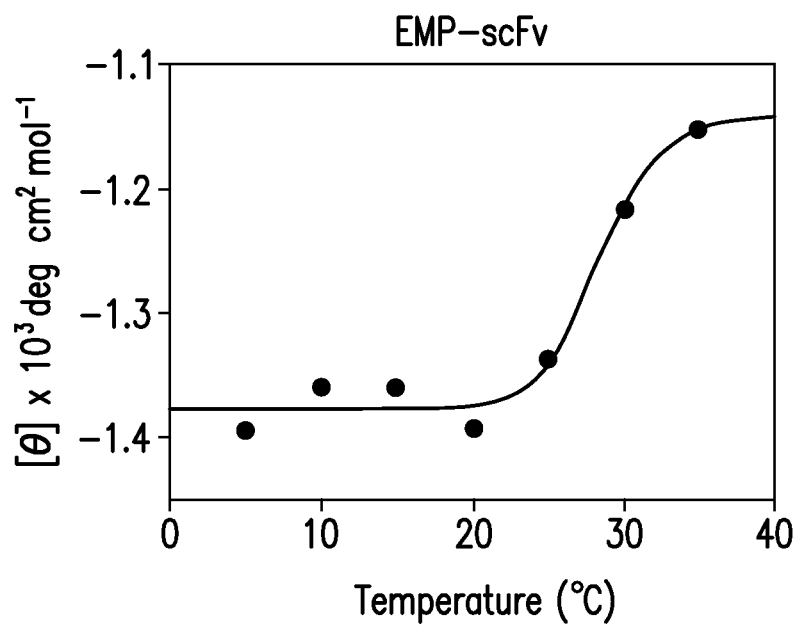
FIG. 2E shows data on the transition profiles monitoring the appearance of the β-turn structure of EMP-scFv.

The transition curves of the EMP demonstrated a typical unfolding/folding model representing a two-state transition (FIG. 2d). The mathematical fitting of the CD data allowed the determination of the transition temperature ($T_t$) resulting from conformational change of EMP as the temperature is increased. The mathematical fitting of the CD data to the van't Hoff equation allowed the determination of the transition temperature ($T_t$) resulting from conformational change of EMP and EMP-scFv as the temperature is increased. The transition temperature was calculated using a linear van't Hoff plot of ln K (equilibrium constant, K, where $K=([\theta]^{obs}-[\theta]^{U})/([\theta]^{F}-[\theta]^{obs})$ as a function of 1/T and from the relation, $T=\Delta H/\Delta S$. $[\theta]^{obs}$ is the experimentally observed CD data, and $[\theta]^{F}$, $[\theta]^{U}$ are the fitted endpoints for the transition (a folded protein at high T, $[\theta]^{F}$, and a unfolded protein at low T, $[\theta]^{U}$, respectively) The $T_t$ calculation indicated the consistent $T_t$ of approximately 26° C. for 198 and 220 nm. In contrast, different $T_t$ of EMP-scFv for the disappearance of the random coil and the appearance of the β-turn structure was clearly obtained from fitting of the CD data at 200 nm (15° C.) and that at 215 nm (28° C.) strongly suggesting the presence of a multi-state transition including conformational change of EMP domain and hydrophobic interaction between the hydrophobic residues on the surface of antibody and the EMP within the fusion protein (FIG. 2e). This thermal transition curve of EMP-scFv also suggests that structural change and hydrophobic collapse in the fusion were completed at temperatures higher than 35° C.

Example 3

Proposed Structural Models of EMP-scFv Fusion Protein

Figure 3A:
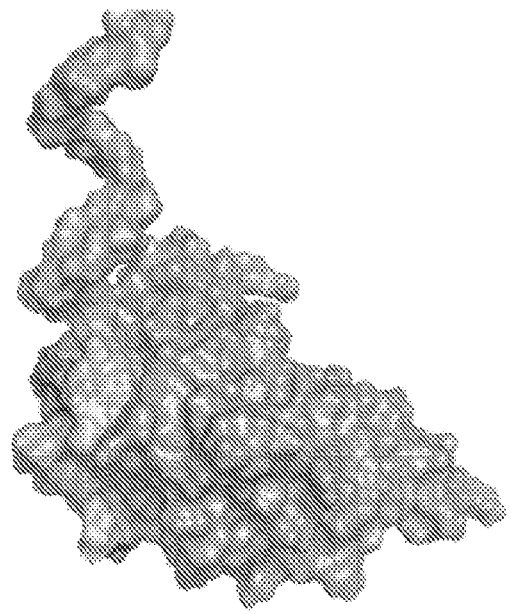
FIG. 3A illustrates a proposed structural model of the EMP-scFv fusion construct after temperature collapse wherein the scFv antibody (grey) is represented as a space-filling model, with the RXD motif in the CDR3 region of the heavy chain highlighted in magenta. This docking solution shows a portion of EMP (green) as a β-spiral which covers the RXD motif such that it can no longer interact with the platelet epitope.
Figure 3B:
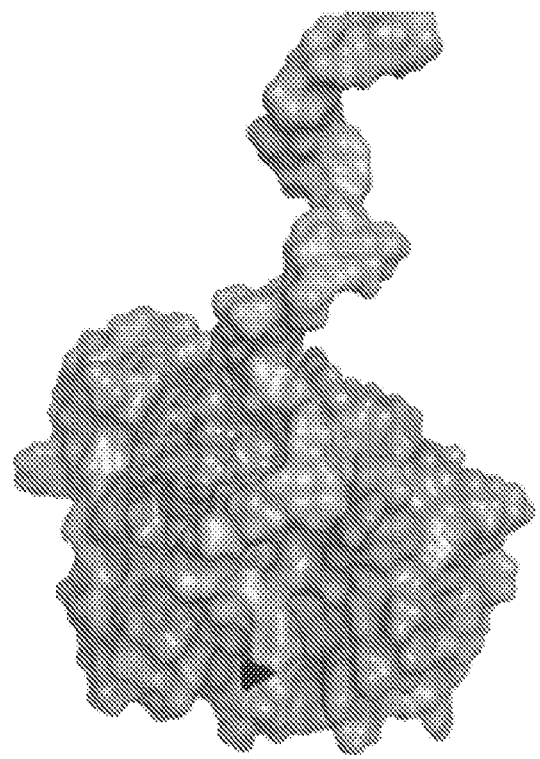
FIG. 3B illustrates a proposed structural model of the EMP-scFv fusion construct after temperature collapse wherein a 90° rotation around the y-axis shows the complimentarily of the β-spiral of EMP for the antibody, particularly when displayed on a larger scale.
Figure 3C:
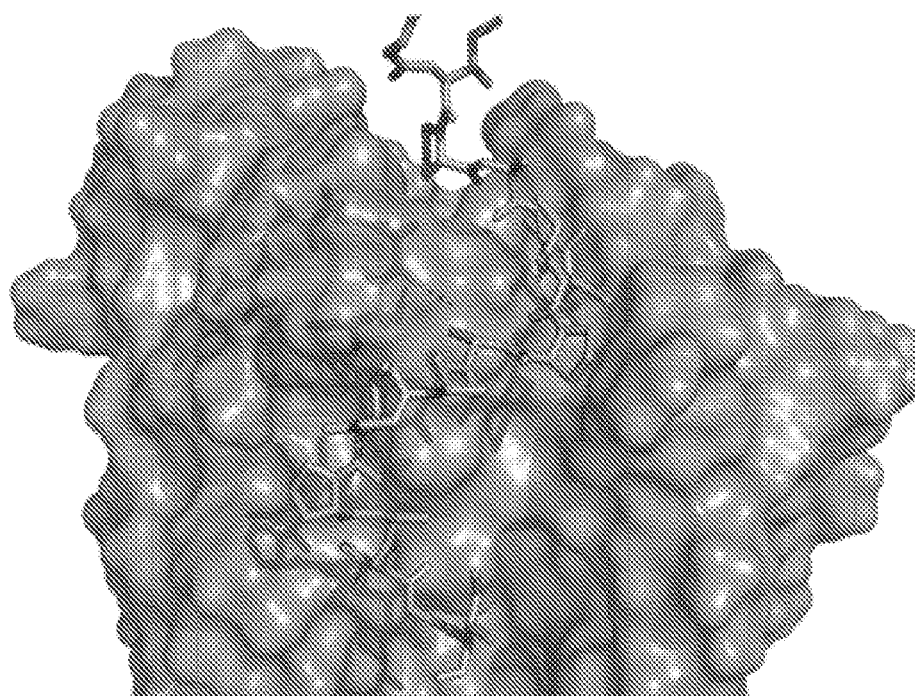
FIG. 3C illustrates a proposed structural model of the EMP-scFv fusion construct after temperature collapse where EMP is shown as green sticks. These figures were constructed in Pymol.

FIG. 3 shows the proposed structural model from one of the top docks for the EMP-scFv fusion construct after the conformational transition has occurred at 37° C. The location of the β-spiral EMP obstructs the RXD motif in the CDR3 region of the heavy chain, which in turn inhibits binding of the scFv to GPIIb/IIIa (FIG. 3a). This is further confirmed by a 90° rotation around the y-axis, which demonstrates the complimentarily of the β-spiral of EMP for the antibody (FIG. 3b), particularly when displayed on a larger scale (FIG. 3c)

Example 4

Figure 4A:
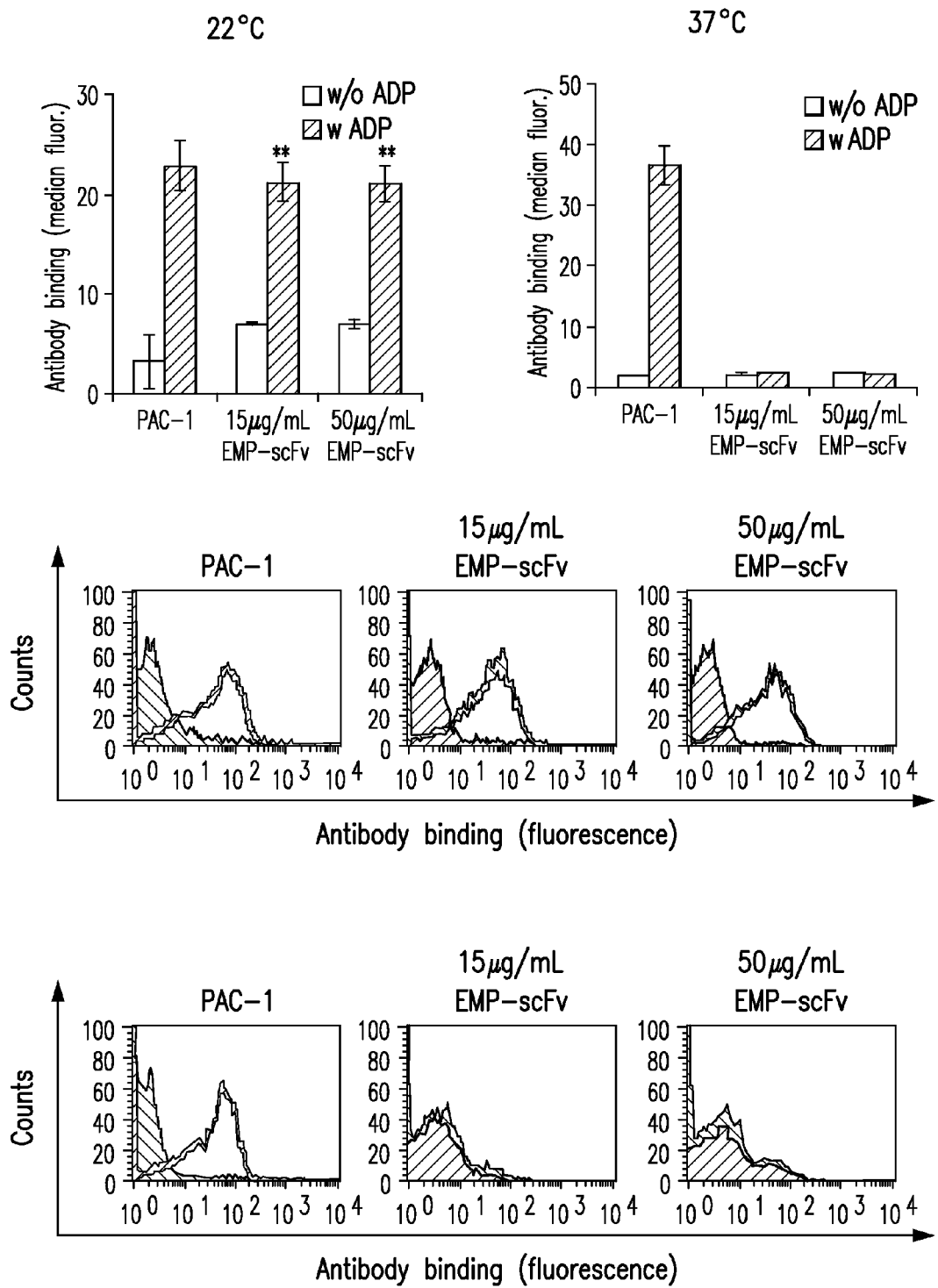
FIG. 4A shows data on temperature-specific binding of EMP-scFv and inhibition of fibrinogen binding to human platelets by EMP-scFv. Bar graphs and histograms represent binding to GPIIb/IIIa at 22° C., but not at 37° C. The results represent the mean±SD of four independent experiments. Asterisks refer to statistically significant differences between mean values (**$p<0.01$, $p<0.001$). Four conditions were tested for the ability of EMP-scFv to inhibit binding of fibrinogen: in the absence of additive (control), in the presence of 10 μg/mL abciximab (abciximab) and in the presence of two concentrations of EMP-scFv (15 μg/mL EMP-scFv and 50 EMP-scFv).

Temperature-Specific Binding of EMP-scFv and Inhibition of Fibrinogen Binding to Human and Mouse Platelets The function of the scFv component of the fusion molecule was evaluated by flow cytometry. A significantly higher level of EMP-scFv binding to human activated platelets was evident when experiments were conducted at 22° C., while the binding of the fusion protein to activated platelets was totally abolished when the temperature of the assay was increased to 37° C. (FIG. 4a). The induction of PAC-1 binding, which is a mAb that specifically binds to the activated GPIIb/IIIa receptor, on platelets treated with 20 μM ADP clearly demonstrates that the cells in both 22° C. and 37° C. experiment were indeed activatable. No binding of the EMP-scFv recombinant protein to resting platelets was detected, regardless of the temperature used in the experiment (FIG. 4a).

In a concentration-dependent manner, EMP-scFv significantly reduced the level of fibrinogen binding to human activated platelets at 22° C., reaching almost the same inhibitory levels as observed with the positive control abciximab (ReoPro®), which is a clinically used humanized Fab fragment blocking GPIIb/IIIa (FIG. 4b). Binding of fibrinogen to activated platelets by EMP-scFv was not inhibited at 37° C. (FIG. 4b). Fibrinogen did not bind to resting platelets regardless of the temperature used (FIG. 4b).

Figure 7A:
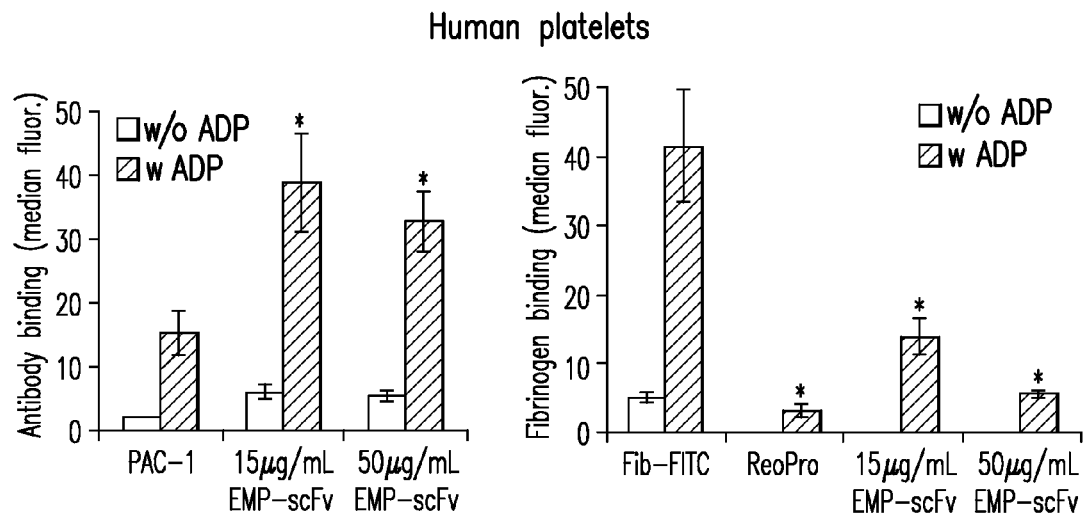
FIG. 7A shows data on the binding of EMP-scFv and inhibition of fibrinogen binding by EMP-scFv to human platelets at 32° C. Bar graphs represent temperature dependent binding of EMP-scFv to activated human platelets at 32° C., and inhibition of fibrinogen binding to human platelets by EMP-scFv at 32° C.
Figure 7B:
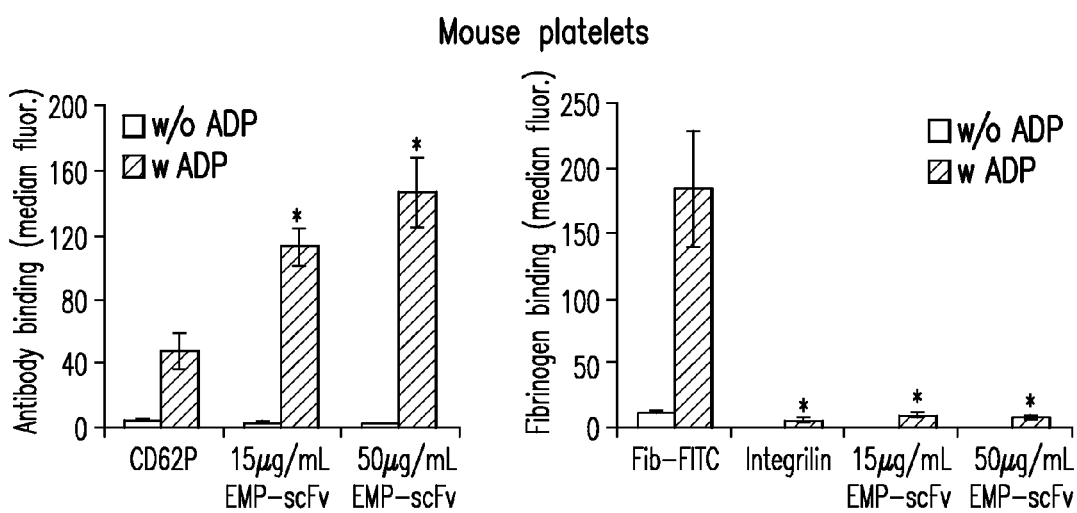
FIG. 7B shows data on the binding of EMP-scFv and inhibition of fibrinogen binding by EMP-scFv to mouse platelets at 32° C. Bar graphs represent temperature dependent binding of EMP-scFv to activated mouse platelets at 32° C., and inhibition of fibrinogen binding to mouse platelets by EMP-scFv at 32° C.

Flow cytometry demonstrated a significant decrease in fibrinogen binding to activated mouse platelets at 22° C. in the presence of EMP-scFv. Eptifibatide (Integrilin®), which is a clinically used small molecular weight GPIIb/IIIa inhibitor, was used as a positive control for the inhibition of fibrinogen binding. Similar to human platelets, the presence of EMP-scFv in the experiments conducted at 37° C. did not affect the binding of fibrinogen to activated mouse platelets. Fibrinogen did not bind to mouse resting platelets regardless of the temperature used in the experiment. Re-warming experiments demonstrated that after binding to activated platelets at 22° C., EMP-scFv did not dissociate from GPIIb/IIIa upon increasing the temperature of the reaction to 37° C. (FIG. 4C). Furthermore, flow cytometry confirmed the ability of EMP-scFv to bind, as well as inhibit the binding of fibrinogen to human (FIG. 7a) and mouse (FIG. 7b) activated platelets at 32° C., a mild form of hypothermia increasingly used to treat out-of-hospital cardiac arrests.

To confirm that the blocking effect observed is due to the binding of the scFv component of the fusion protein to the activated platelets, we generated EMP alone following the same approach used to purify EMP-scFv and tested its binding to platelets. After generating a protein of approximately 35 kDa, our in vitro flow cytometry experiments demonstrated that EMP alone did not bind to either resting or activated platelets regardless of the temperature used in the experiments. Furthermore, flow cytometry demonstrated that EMP-scFv did not activate platelets, as the fusion protein had no effect on binding of PAC-1 or P-selectin expression.

Example 5

Figure 5A:
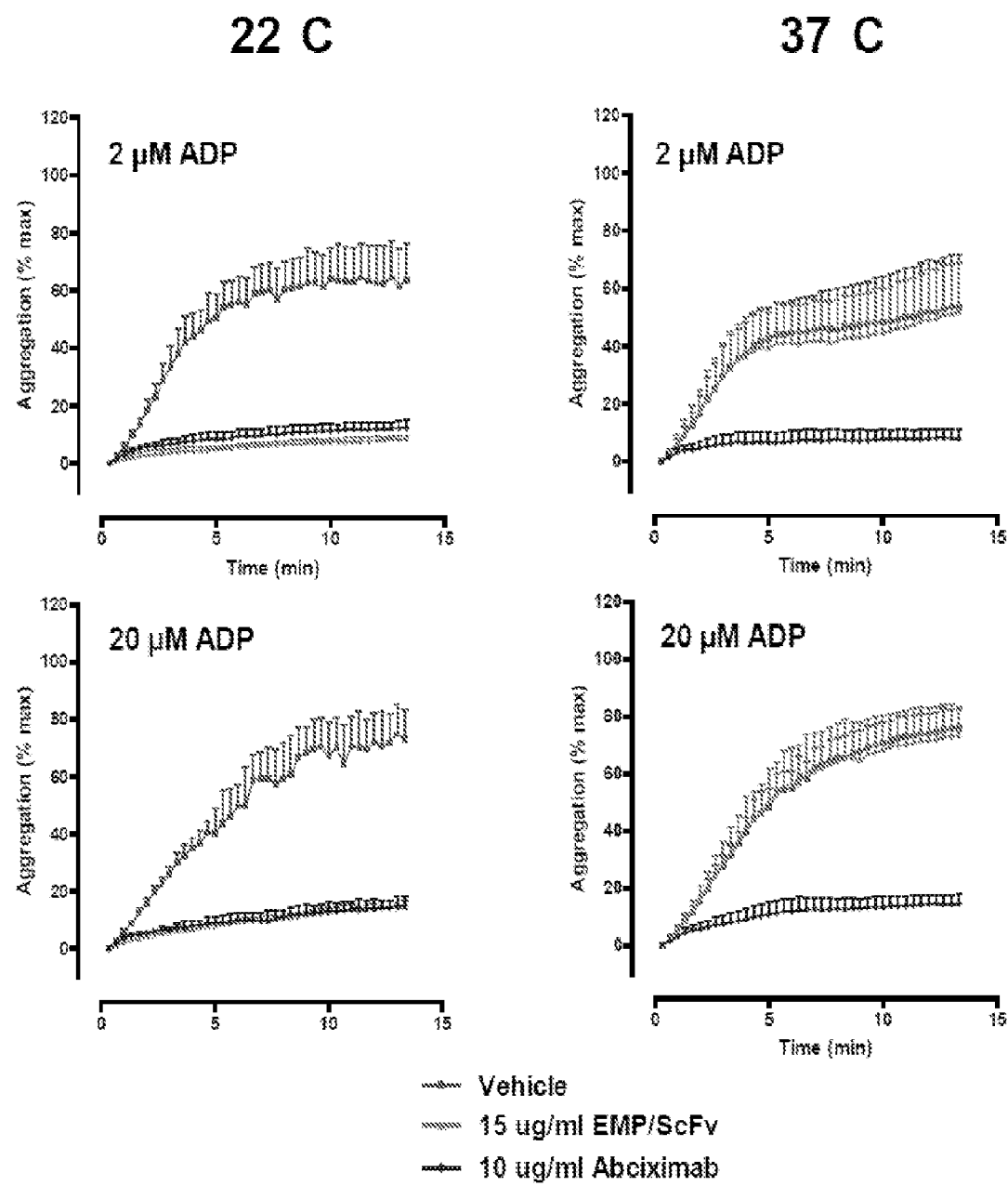
FIG. 5A shows data on the effects of EMP-scFv on human platelet aggregation at different temperatures. Light transmission aggregometry demonstrates the ability of EMP-scFv to inhibit aggregation of platelets treated with ADP at 22° C., but not at 37° C. The results represent the mean±SD of four independent experiments.
Figure 5B:
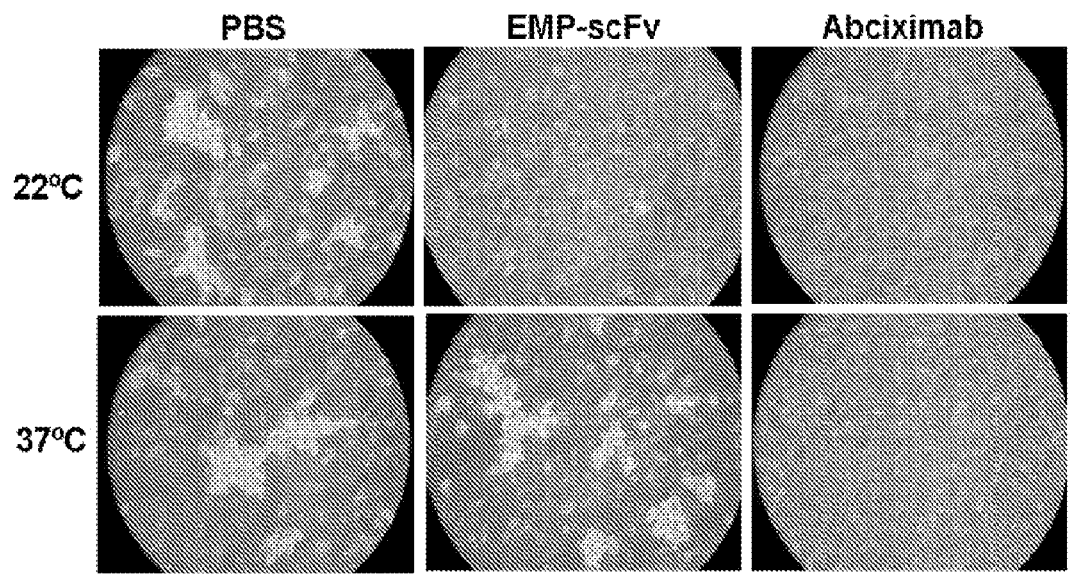
FIG. 5B shows microscopic images that activated platelets aggregate in the absence of EMP-scFv at 22° C., but not at 37° C., while the addition of abciximab abolishes aggregation at both temperatures. At 37° C. activated platelets aggregate regardless of the presence or absence of EMP-scFv. Typical examples out of 3 experiments are given.

Temperature-Specific Inhibition of Platelet Aggregation by EMP-scFv and Temperature-Dependent Binding of EMP-scFv to Platelet Aggregates Under Physiological Flow Conditions As a functional evaluation of platelets, effective inhibition of ADP-driven platelet aggregation by EMP-scFv at 22° C., but not at 37° C. was demonstrated using a 96-well plate-based light transmission aggregometry approach (FIG. 5a). To further assess the effect of EMP-scFv on platelet aggregation, aggregate formation was directly visualized in microscopy. EMP-scFv inhibited aggregation of activated human platelets at 22° C. but not at 37° C. (FIG. 5b). Flow chamber experiments demonstrated that hypothermic temperatures induced binding of EMP-scFv to platelet aggregates.

Example 6

Temperature-Specific In Vivo Antithrombotic Effects of EMP-scFv

In vivo experiments in a mouse thrombosis model were performed. As a first step, flow cytometry using mouse whole blood was performed to show that EMP-scFv binds to activated murine platelets at 22° C., but not at 37° C. EMP-scFv did not bind to resting mouse platelets at either 22° C. or 37° C. Furthermore, flow cytometry demonstrated a significant decrease in fibrinogen binding to activated mouse platelets at 22° C. and 32° C. in the presence of EMP-scFv, while the fusion protein EMP-scFv had no effect on the binding of fibrinogen to mouse activated platelets in the experiments conducted at 37° C.

Figure 6:
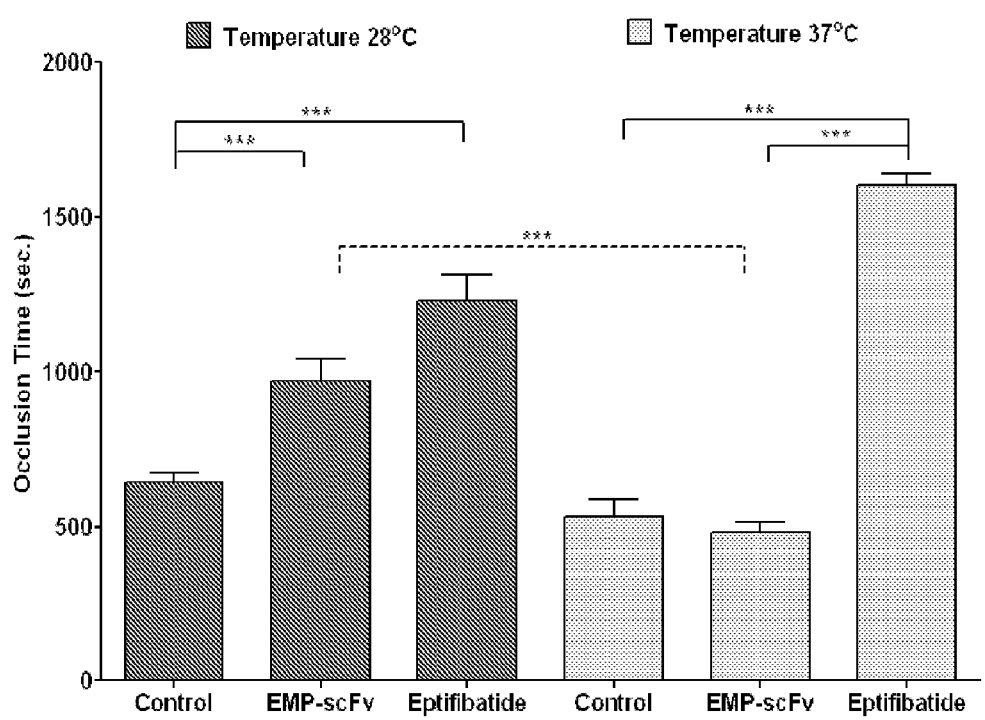
FIG. 6 shows data on the anti-thrombotic effects of EMP-scFv by activation-specific inhibition of GPIIb/IIIa in mice. Thrombus development was induced in carotid arteries by local vessel injury using ferric chloride. Arterial occlusion times in mice injected with EMP-scFv at 28° C. are significantly higher when compared to the control group investigated at the same temperature, as well as to the experiments conducted at 37° C. The results represent the mean of ±SD of at least 5 animals per group. Asterisks refer to statistically significant differences between mean values (***$p<0.001$).

To demonstrate the advantages of temperature-dependent activation-specific GPIIb/IIIa blockade by EMP-scFv in vivo, a ferric chloride-induced mouse carotid artery thrombosis model was chosen. The EMP-scFv significantly prolonged the occlusion time in mice injected with the fusion protein at 28° C., compared to the control group, showing a similar platelet-inhibitory effect to that observed with eptifibatide (FIG. 6). At 37° C., the occlusion time between the control group and the group treated with EMP-scFv remained unchanged (FIG. 6).

The temperature-dependant anti-thrombotic effects of EMP-scFv in a model of jugular venous thrombosis was examined. The percentage of initial blood flow showed significantly higher levels of blood flow 15 minutes after the injury in mice injected with EMP-scFv at 28° C., compared to the control group and those experiments conducted at 37° C.

The effects on the jugular venous blood flow of EMP-scFv at 28° C. are comparable to the clinically used GPIIb/IIIa blocker eptifibatide

METHODS

Generation of the EMP-scFv Fusion Construct

Single-stranded oligonucleotides encoding the forward and reverse strands of monomer, (IPAVG)$_5$ [ATT CCG GCT GTT GGT ATC CCA GCT GTT GGT ATC CCA GCT GTT GGC ATT CCG GCT GTA GGT ATC CCG GCA GTG GGC] (SEQ ID NO:6) were chemically synthesized (Sigma Genosys, Inc.) with BamH I and Hind III overhangs and annealed to generate double-stranded oligonucleotides. The double stranded DNA cassettes were purified by agarose gel electrophoresis (4% GTG NuSieve agarose, 1×TBE buffer), phosphorylated and inserted into pZErO-1 cloning vector. Plasmid containing monomer DNA was propagated in the *E. coli* strain Top 10F' and the inserts were screened and verified by DNA sequencing. Monomeric genes encoding (IPAVG)$_5$ were sequentially digested with restriction enzymes, Bbs I and BsmB I, respectively, and isolated by agarose gel electrophoresis (4% GTG NuSieve agarose). The purified DNA monomers were concatamerized in a head-to-tail method via T4 DNA ligase. This multimerization of DNA monomers afforded to produce various sizes of multimers. A clone encoding sixteen repeats of the EMP monomer was isolated from insertion of multimer mixtures into the BsmB I site of the original plasmid containing the monomer DNA.

In order to clone the EMP gene into pET39b(+) expression vector, a cloning vector was modified such that the polylinker could accommodate the multimer at the Bbs I sites and add a short linker sequence of GGGGS (see SEQ ID NO: 12) to the 3' end of the multimer. EMP gene of the appropriate size in pZErO-1 was liberated by restriction digestion with Bbs I and BsmB I, respectively, and inserted into the internal two Bbs I sites of a polylinker in pZErO-2. A recombinant clone encoding sixteen repeats of monomer and short linker sequence was cloned into the pET39b(+) vector using Nco I restriction sites, and then sub-cloned in pHOG-21 bacterial expression vector already containing single-chain antibody (scFv) cDNA incorporating His(6)-tag sequence, resulting in a final fusion construct outlined in FIG. 1. The pHOG-21 expression vector contains a pelB leader peptide which allows for periplasmic localization of the recombinant protein within the bacteria. This bacterial expression vector is also characterized by the presence of a His(6)-tag for the Ni$^{2+}$ which facilitates purification and detection of recombinant proteins. It also contains an ampicillin resistance gene used for selection.

The nucleic acid sequence that expresses the conjugate polypeptide comprising SEQ ID NOs: 7-10 in respective numerical order. SEQ ID NO:7 encodes the elastin mimetic peptide SEQ ID NO: 11, SEQ ID NO:8 encodes the linker SEQ ID NO: 12, SEQ ID NO:9 encodes the scFv single chain antibody SEQ ID NO: 13, wherein the underlined portion is the RGD binding site, SEQ ID NO:10 encodes the histidine-tag followed by the stop codon (double underline). In certain embodiments, the disclosure relates to isolated non-naturally occurring nucleic acids and recombinant expression systems comprising the nucleic acids encoding the polypeptides disclosed herein.

(SEQ ID NO: 7)

```
ATGGCGGTTCCAGCTGTTGGTATTCCGGCTGTTGGTATCCCAGCTGTTGGTATCC

CAGCTGTTGGCATTCCGGCTGTAGGTATCCCGGCAGTGGGCATTCCGGCTGTTGG

TATCCCAGCTGTTGGTATCCCAGCTGTTGGCATTCCGGCTGTAGGTATCCCGGCA

GTGGGCATTCCGGCTGTTGGTATCCCAGCTGTTGGTATCCCAGCTGTTGGCATTC

CGGCTGTAGGTATCCCGGCAGTGGGCATTCCGGCTGTTGGTATCCCAGCTGTTGG

TATCCCAGCTGTTGGCATTCCGGCTGTAGGTATCCCGGCAGTGGGCATTCCGGCT

GTTGGTATCCCAGCTGTTGGTATCCCAGCTGTTGGCATTCCGGCTGTAGGTATCC

CGGCAGTGGGCATTCCGGCTGTTGGTATCCCAGCTGTTGGTATCCCAGCTGTTGG

CATTCCGGCTGTAGGTATCCCGGCAGTGGGCATTCCGGCTGTTGGTATCCCAGCT

GTTGGTATCCCAGCTGTTGGCATTCCGGCTGTAGGTATCCCGGCAGTGGGCATTC

CGGCTGTTGGTATCCCAGCTGTTG

GTATCCCAGCTGTTGGCATTCCGGCTGTAGGTATCCCGGCAGTGGGCATTCCGGC

TGTTGGTATCCCAGCTGTTGGTATCCCAGCTGTTGGCATTCCGGCTGTAGGTATC

CCGGCAGTGGGCATTCCGGCTGTTGGTATCCCAGCTGTTGGTATCCCAGCTGTTG

GCATTCCGGCTGTAGGTATCCCGGCAGTGGGCATTCCGGCTGTTGGTATCCCAGC

TGTTGGTATCCCAGCTGTTGGCATTCCGGCTGTAGGTATCCCGGCAGTGGGCATT

CCGGCTGTTGGTATCCCAGCTGTTGGTATCCCAGCTGTTGGCATTCCGGCTGTAG

GTATCCCGGCAGTGGGCATTCCGGCTGTTGGTATCCCAGCTGTTGGTATCCCAGC

TGTTGGCATTCCGGCTGTAGGTATCCCGGCAGTGGGCATTCCGGCTGTTGGTATC

CCAGCTGTTGGTATCCCAGCTGTTGGCATTCCGGCTGTAGGTATCCCGGCAGTGG

GCATTCCGGCTGTTGGTATCCCAGCTGTTGGTATCCCAGCTGTTGGCATTCCGGC
```

-continued

TGTAGGTATCCCGGCAGTGGGCATTCCGGCTGTTGGTATCCCAGCTGTTGGTATC

CCAGCTGTTGGCATTCCGGCTGTAGGTATTCCA (SEQ ID NO: 8)
GGTGGCGGTGGCTCCATG (SEQ ID NO: 9)
ATGGCGGAGGTGCAGCTGGTGGAGTCTGGGGGAGGCTTGGTACAGCCTGGGGGG

TCCCTGAGACTCTCCTGTGCAGCCTCTGGATTCATGTTTAGCAGGTATGCCATGA

GCTGGGTCCGCCAGGCTCCAGGGAAGGGGCCAGAGTGGGTCTCAGGTATTAGTG

GTAGTGGTGGTAGTACATACTACGCAGACTCCGTGAAGGGCCGGTTCACCGTCTC

CAGAGACAATTCCAAGAACACGCTGTATCTGCAAATGAACAGCCTGAGAGCCGA

GGACACTGCCGTGTATTACTGTGCGAGAATTTTTACGCATCGGTCG<u>CGTGGTGAC</u>

GTCCCGGACCAAACTAGCTTTGACTACTGGGGCCAGGGAACCCTGGTCACCGTC

TCCTCAGGGAGTGCATCCGCCCCAAAGCTTGAAGAAGGTGAATTTTCAGAAGCA

CGCGTAAGCTCTGAACTGACTCAGGACCCTGCTGTGTCTGTGGCCTTGGGACAGA

CAGTCAGGATCACATGCCAAGGAGACAGCCTCAGAAACTTTTATGCAAGCTGGT

ACCAGCAGAAGCCAGGACAGGCCCCTACTCTTGTCATCTATGGTTTAAGTAAAA

GGCCCTCAGGGATCCCAGACCGATTCTCTGCCTCCAGCTCAGGAAACACAGCTTC

CTTGACCATCACTGGGGCTCAGGCGGAAGATGAGGCTGATTATTACTGCCTGCTC

TACTATGGTGGTGGTCAGCAGGGAGTGTTCGGCGGAGGGACCAAGCTGACCGTC

CTACGTCAGCCCAAGGCTGCCCCCTCGGTCACTCTGTTCCCGCCCTCTTCTGCGG

CCGCTGGATCCGAACAAAAGCTGATCTCAGAAGAAGACCTAAACTCA (SEQ ID NO: 10)
CATCACCATCACCATCAC<u>TAA</u>

(SEQ ID NO: 11)
MAVPAVGIPAVGIPAVGIPAVGIPAVGIPAVGIPAVGIPAVGIPAVGIPAVGIPA

VGIPAVGIPAVGIPAVGIPAVGIPAVGIPAVGIPAVGIPAVGIPAVGIPAVGIPA

VGIPAVGIPAVGIPAVGIPAVGIPAVGIPAVGIPAVGIPAVGIPAVGIPAVGIPA

VGIPAVGIPAVGIPAVGIPAVGIPAVGIPAVGIPAVGIPAVGIPAVGIPAVGIPA

VGIPAVGIPAVGIPAVGIPAVGIPAVGIPAVGIPAVGIPAVGIPAVGIPAVGIPA

VGIPAVGIPAVGIPAVGIPAVGIPAVGIPAVGIPAVGIPAVGIPAVGIPAVGIPA

VGIPAVGIPAVGIPAVGIPAVGIPAVGIPAVGIPAVGIP (SEQ ID NO: 12)
GGGGSM (SEQ ID NO: 13)
MAEVQLVESG GGLVQPGGSL RLSCAASGFM FSRYAMSWVR QAPGKGPEWVSG

ISGSGGSTY YADSVKGRF TVSRDNSKN TLYLQMN SLRAEDTAV YYCARIFT

HRS<u>RGD</u>VPD QTSFDYWGQ GTLVTVSSG SASAPKLEE GEFSEARVS SELTQDPAV

SVALGQTVRIT CQGDSLRNFY ASWYQQKPG QAPTLVIYG LSKRPSGIPDRF

SASSSGNTASLTIT GAQAEDEADYYCL LYYGGGQQ GVFGGGTKLTVLR

QPKAAPSVTLFPPSSAAAGSEQKLISEEDLNS

Expression of EMP-scFv Construct in *E. coli* and Protein Purification

*E. coli* (TG1) cells were transformed with the pHOG-21 plasmid described above and plated on an agar plate containing 100 μg/mL ampicillin. Starter culture was established by inoculating a single colony into 10 mL of LB media containing 100 μg/mL ampicillin and growing it overnight in a 37° C. incubator at 200 rpm. The following day, starter culture was transferred into 1 L of fresh LB containing 100 μg/mL ampicillin and the cultures shaken at 220 rpm for approximately 4-6 hours until an OD (600 nm) of ~0.6 was reached, followed by the addition of IPTG to a final concentration of 1 mM for induction of scFv production and incubated at 37° C. with 200 rpm for 6-8 hours. For purification of insoluble protein from whole cell extract, bacteria were harvested by centrifugation at 5000 rpm for 15 min at 4° C. Pelleted bacteria were resuspended in 5 mL of cold 1× BugBuster® (Novagen) solution/g pellet and incubated for 15 min at room temperature with gentle shaking. After an additional centrifugation at 15 000 rpm for 20 min at 4° C., the supernatant was discarded and inclusion bodies containing insoluble protein resuspended in 15 mL solution containing 1:10 dilution of ice cold Bug-Buster®.

The resuspended inclusion bodies were incubated at room temperature for 15 minutes with gentle shaking, before centrifuging at 5000 rpm for 15 min at 4° C. The wash step was repeated 4 more times, followed by the resuspension of the inclusion body pellet in buffer B (8 M urea, 100 mM $NaH_2PO_4$, 100 mM Tris HCl, pH 8). The insoluble fraction was purified by passing through a purification column previously layered with 600 µL of $Ni^{2+}$-Agarose beads (Qiagen). The fraction was applied through the same column 4 times to ensure the maximal binding of His(6)-tagged proteins. The column was washed with 7 mL of buffer B, 7 mL of buffer C (8 M urea, 100 mM $NaH_2PO_4$, 100 mM Tris HCl, pH 6.3) and 7 mL of buffer D (8 M urea, 100 mM $NaH_2PO_4$, 100 mM Tris HCl, pH 5.9). Finally, EMP-scFv fusion proteins were eluted with buffer D (8 M urea, 100 mM $NaH_2PO_4$, 100 mM Tris HCl, pH 4.5) in approximately 8-10 separate fractions of 600 µL.

The proteins were refolded using 1 L re-folding (RF) buffer (100 mM $NaH_2PO_4$, 10 mM Tris-HCl, pH 7.4) at 4° C. with gentle stirring, where the concentration of urea was reduced every two hours from 6 M, 4 M and to 2 M, before finally incubating the protein samples in 4 L of 1×PBS overnight at 4° C. The concentration of dialyzed fractions was determined using BCA assay, and the integrity of the protein was assessed via SDS-PAGE and Western Blotting under reducing conditions. Proteins were transferred onto an Immobilon P membrane (Millipore Corporation) for immunoblotting. After blocking the membrane overnight with phosphate buffered saline containing 0.2% Tween20 (PBS-Tween) and 1% BSA, a HRP-labelled anti-His(6)-antibody (Roche) was added (dilution 1:2000) and incubated for 2 hours at room temperature. The membrane was washed several times with PBS-Tween buffer. Visualization of peroxidase activity was achieved by addition of SuperSignal® Chemiluminescent Substrate (Pierce) on a ChemiDoc XRS® (BioRad).

Circular Dichroism (CD) and Thermal Transition Profile Monitoring

Circular dichroism (CD) spectra were recorded on a Jasco J-810 spectropolarimeter equipped with a PFD-425S Peltier temperature control unit in 0.1 cm sealed quartz cells at concentrations of 7.5 µM (EMP), 8.4 µM (scFv) and 4.1 µM (EMP-scFv) in 50 mM sodium phosphate buffer, pH 7.4. Temperature/wavelength CD-scans were performed within the temperature range from 5° C. to 35° C. with equilibration for 10 min at each temperature. Spectra were obtained from 260 to 190 nm at a resolution of 0.5 nm and at a scanning speed of 50 nm/min. The CD curves represented the average of five measurements and were smoothed using the means-movement method on the interval analysis of the spectral manager program. CD data are reported as mean residue ellipticity ($[\theta]$, deg cm$^2$ dmol$^{-1}$). Thermal transition curves were plotted by the mean residue ellipticity as a function of temperature for the disappearance of the random coil and the appearance of the β-turn structure.

Flow Cytometry

Human blood was collected by venipuncture with a 21-gauge butterfly needle from healthy volunteers and anticoagulated with citric acid. Platelet-rich plasma (PRP) was obtained by centrifugation (GS-6R centrifuge, Beckman Coulter) at 100×g at room temperature for 10 min.

Mouse blood was collected by intracardiac puncture with a 27-gauge needle from C57BL/6 mice and anticoagulated with non-fractionated heparin (20 U/mL). A volume of 50 µl was washed with 1 mL modified Tyrode's buffer (150 mM NaCl, 2.5 mM KCl, 1.2 mM $NaHCO_3$, 0.1% BSA, 0.1% Glucose) and centrifuged at 1200×g for 6 min. The supernatant was discarded and the pellet was resuspended in 1 mL modified Tyrode's buffer containing 2 mM $MgCl_2$ and 2 mM $CaCl_2$.

Human PRP was diluted 1/50 in modified Tyrode's buffer containing 2 mM $MgCl_2$ and 2 mM $CaCl_2$. Platelets were either activated by addition of 20 µM ADP, or non activated, followed by the incubation with 15 and 50 µg/mL EMP-scFv fusion protein or EMP at 22° C., 32° C. and at 37° C. for 15 min. Mouse platelets were either pre-activated for 10 min by addition of 0.1 U/mL thrombin (Enzyme Research Laboratories), or non activated, before the incubation with 15 and 50 µg/mL of EMP-scFv fusion protein at 22° C., 32° C. or 37° C. for 15 min. In both, human and mouse samples, EMP-scFv was detected via 15 min in-dark incubation with secondary antibody (Penta-His Alexa Fluor 488, Qiagen) directed against the His(6)-tag of the single-chain antibody.

Fibrinogen binding to human activated platelets in the presence of EMP-scFv was determined with a polyclonal rabbit anti-human fibrinogen FITC-labelled antibody (Dako-Cytomation), while the effects of EMP-scFv on fibrinogen binding to mouse platelets were determined using FITC-conjugated rabbit anti-fibrinogen polyclonal antibody (Cemfret). Fluorescence detection was performed as described above. Samples were measured in a FACSCalibur® flow cytometer (Becton Dickinson), after fixation with 1× Cell-FIX® (Becton Dickinson).

In re-warming experiments, activated and non-activated diluted human PRP was incubated with 15 and 50 µg/mL of EMP-scFv for 15 minutes at 22° C., followed by a 15-min in dark incubation with secondary Penta-His Alexa Fluor 488 antibody. Half of the reaction was then fixed with 1× Cell FIX, while the other half was incubated at 37° C. for either 15 or 30 minutes, before being fixed and measured in FACS.

Effects of EMP-scFv on platelet activation were addressed by incubating human diluted PRP with 15 and 50 µg/mL of EMP-scFv at 22° C. for 15 minutes, followed by the addition of either PAC-1 or CD62P antibodies and in-dark incubation for 15 minutes. The reactions were fixed and levels of PAC-1 binding and P-Selectin expression analysed in FACS.

Platelet Aggregometry and Targeting of EMP-scFv to Platelet Aggregates under Physiological Flow Conditions at Different Temperatures Light transmission aggregometry was performed using a Biorad Benchmark plate reader. After incubation of human PRP with EMP-scFv (15 µg/mL), vehicle (PBS) or the GPIIb/IIIa blocker abciximab (10 µg/mL) (Reopro®, Eli Lilly, Indianapolis, U.S.A.) for 10 minutes at different temperatures, the aggregation was induced by the addition of 2 or 20 µM ADP with vigorous stirring in a 96-well plate. The absorbance was determined at 595 nm every 15 seconds for 16 minutes between vigorous shaking at 22° C. and 37° C.

For the microscopic analysis of platelet aggregates at different temperatures, non-diluted human PRP was placed onto a glass slide and ADP was added to a final concentration of 20 µM, in the presence and absence of EMP-scFv (50 µg/mL).

Abciximab was used as a positive control at a concentration of 10 μg/mL. The experiments were conducted at 22° C. and 37° C. Phase contrast microscopy images were taken using an Olympus CKX41 microscope.

Temperature-dependent binding of EMP-scFv to platelet aggregates was analysed using a flow chamber system. Vitrotubes rectangular capillaries (0.20×2.0 mm) were washed with 70% ethanol, dried, and coated overnight with 10 μg/ml of collagen (Collagen Reagent Horm Nycomed). Liquid was entered into the capillary via capillary drag. Capillaries were blocked for 1 hour with 1% BSA and then washed with PBS. The capillary was connected on the one end to a reservoir and on the other end to a Harvard medical pump by tubing. Before connecting the capillary all tubes were flushed with PBS in order to avoid air bubbles entering the capillary. PRP was then drawn into the capillary and numerous platelet aggregates were formed within 10 minutes. The capillary was then washed with PBS via the pump. In the meantime, the EMP-scFv (50 μg/mL) was incubated with PENTA-HIS Alexa Fluor 488 (Qiagen) antibody for 10 minutes in a final volume of 1 mL, and then drawn into the capillary containing platelet aggregates at physiological flow rate of $60s^{-1}$. The capillary was then imaged with a 20× magnification objective, after which DIC and fluorescent images were captured using Olympus IX81 microscope with XM10 camera. The experiments were conducted at 22° C. and 37° C.

In Vivo Functional Evaluation of Antithrombotic Efficacy of EMP-scFv at Different Temperatures C57BL/6 mice weighing from 20-25 g were used. Care and use of laboratory animals followed the national guidelines and were approved by the institutional animal care and ethics committees. Mice were anesthetized with isoflurane, following an intra-peritoneal injection with ketamine (100 mg/kg BW) and xylazine (20 mg/kg BW). The body core temperature was monitored with a digital thermometer, and controlled at either 28° C. or 37° C. with a thermal pad (Temperature Controller TR-200, Fine Science Tools Inc.). Reducing the body temperature to 28° C. was achieved by a gradual drop, at a rate of 0.3-0.4° C./min. The mice on the thermal pad were placed under a dissecting microscope (SZ61, Olympus). An incision of the skin was made directly on the top of trachea, and vessels used for experiment were bluntly isolated from surrounding tissues. A catheter was cannulated into the right-side of the Jugular vein, and all administrations were injected into the blood flow via the cannula. Either EMP-scFv, (4.25 μg/g body weight), eptifibatide (0.18 μg/g) or saline (5 μl/g body weight) were administered 5 min prior to induction of the injury on the vessel. Thrombosis on either carotid artery or jugular vein was induced by applying a piece of filter paper (1×2 mm, GB003, Schleicher & Schuell) saturated with ferric chloride (10% solution) (Sigma) beneath the isolated vessel and removed after three minutes. A piece of Parafilm was laid to prevent the injury on surrounding tissue. After rinsing with normal saline, a nano-Doppler flow probe (0.5 VB, Transonic) was then positioned over the vessel and the blood flow rate (ml/min) was measured by a transit-time perivascular flow-meter (TS420, Transonic Systems Inc.). The carotid artery thrombotic occlusion was considered to occur when flow decreased to 0.0±0.2 mL/min, a range corresponding to the accuracy of the system as specified by the manufacturer. Jugular vein blood flow was recorded 15 minutes after induction of injury in mice pre-treated with EMP-scFv, eptifibatide or saline. The blood flow recorded at 1 minute was considered as the initial blood flow rate. The percentage of blood flow rate at 15 minutes over the initial flow rate was compared among different administration groups.

---

The invention claimed is:

1. A conjugate polymer comprising a) a temperature-sensitive polypeptide comprising a repeating IPAVG (SEQ ID NO:23) sequence, wherein the polypeptide takes on a beta-sheet structure at a transition temperature of greater than 28 degrees Celsius and b) an single-chain antibody that binds to GPIIb/IIIa.

2. The conjugate of claim 1, wherein the conjugate binds GPIIb/IIIa at 32° C. or less than 32° C., but not at normal human body temperature.

3. The conjugate of claim 1, wherein the repeating IPAVG (SEQ ID NO: 23) sequence repeats more than 5 times.

4. The conjugate of claim 1, wherein the repeating IPAVG (SEQ ID NO: 23) sequence is SEQ ID NO: 11.

5. The conjugate of claim 1, wherein the single-chain antibody comprises a RGD sequence.

6. The conjugate of claim 1, wherein the single-chain antibody comprises SEQ ID NO: 13.

7. The conjugate of claim 1, wherein the conjugate further comprises a linker comprising polyglycine.

8. The conjugate of claim 1, wherein the conjugate further comprises SEQ ID NO: 12.

* * * * *